United States Patent

Kelleher

[11] Patent Number: 5,810,876
[45] Date of Patent: Sep. 22, 1998

[54] FLEXIBLE FORCEPS DEVICE

[75] Inventor: Brian S. Kelleher, La Jolla, Calif.

[73] Assignee: Akos Biomedical, Inc., San Diego, Calif.

[21] Appl. No.: 538,453

[22] Filed: Oct. 3, 1995

[51] Int. Cl.⁶ .................................................. A61B 17/28
[52] U.S. Cl. ......................... 606/205; 606/207; 606/170
[58] Field of Search ..................................... 606/205, 206, 606/207, 209, 170, 171, 190, 174, 167, 751, 752

[56] References Cited

U.S. PATENT DOCUMENTS

| 4,763,668 | 8/1988 | Macek et al. | 606/206 |
| 5,228,451 | 7/1993 | Bales et al. | 606/205 |
| 5,254,130 | 10/1993 | Poncet et al. | 128/751 |
| 5,439,478 | 8/1995 | Palmer | 606/205 |
| 5,573,546 | 11/1996 | Nakao | 128/751 |

Primary Examiner—Michael Powell Buiz
Assistant Examiner—Kevin Truong
Attorney, Agent, or Firm—Merle W. Richman, III

[57] ABSTRACT

A flexible forceps device comprises a distal end to be inserted into a patient, a proximal end to remain outside the patient and a flexible, elongated body extending between the ends. The flexible body has at least one lumen and may have a smooth, sealed external surface. An effector assembly is attached to the distal end and includes a support piece and at least one movable element. A control assembly is attached to the proximal end and includes a push-pull mechanism. A coaxial actuating assembly extending through the lumen of the flexible body consists of a flexible tube having a lumen, with a control wire slidably disposed within the lumen of the tube. The tube provides a flexible, yet relatively incompressible column support between the effector assembly and control assembly. The proximal end of the control wire is attached to the push-pull mechanism and the distal end is linked to the movable elements, whereby operation of the control assembly moves the movable elements relative to the support piece. The coaxial actuating assembly undergoes a relatively small change in bending stiffness when the control wire is pushed or pulled, resulting in little displacement of the effector assembly relative to the control assembly during operation of the control assembly.

137 Claims, 11 Drawing Sheets

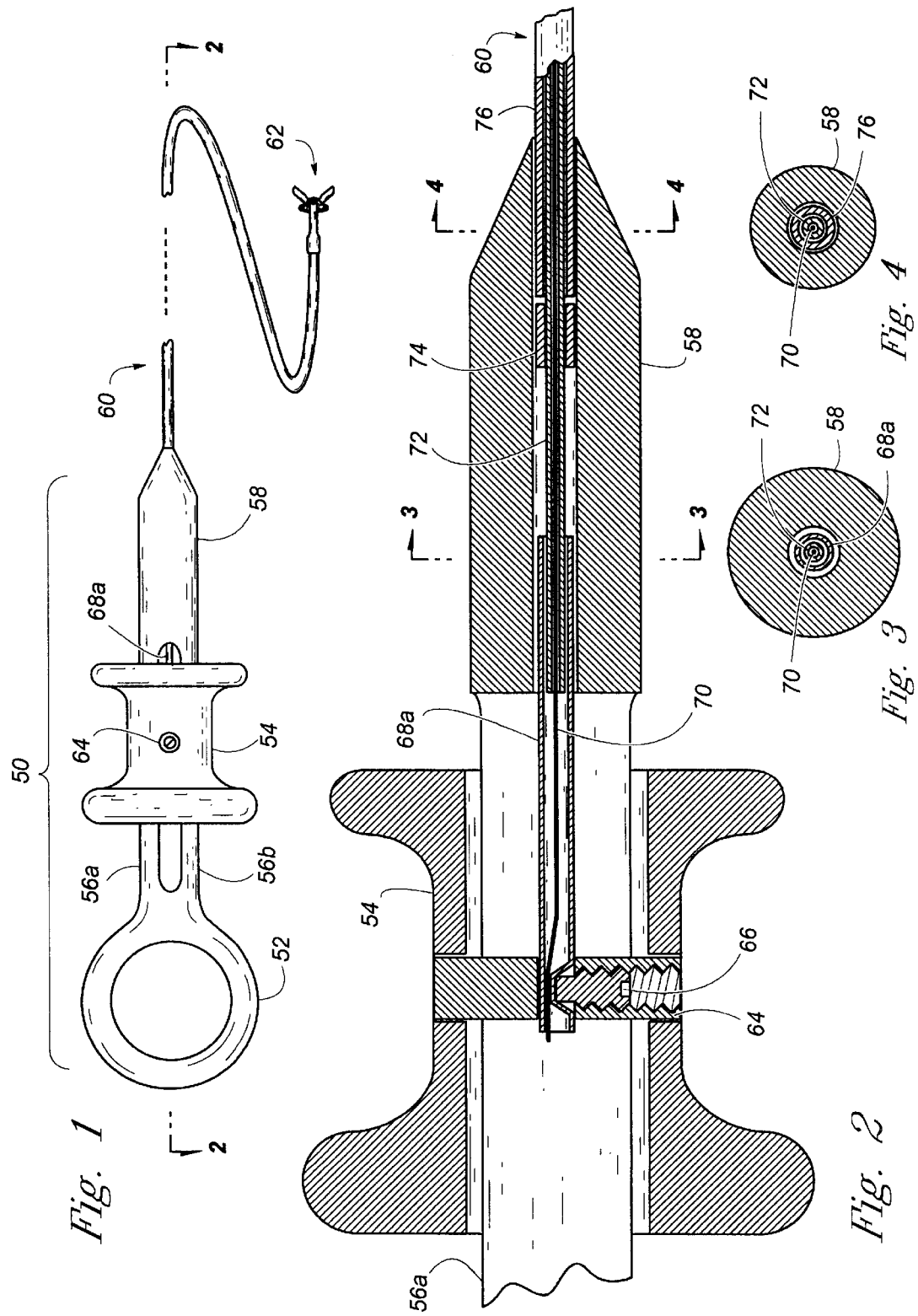

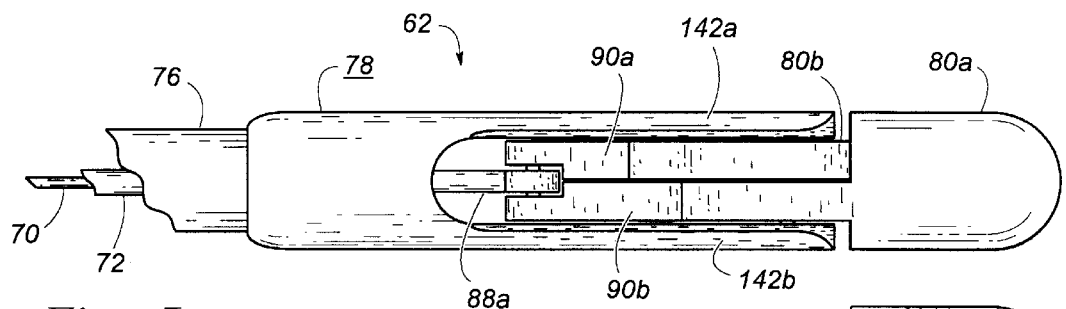
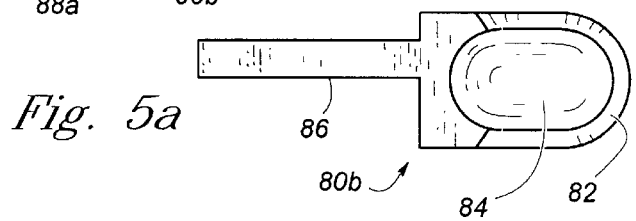
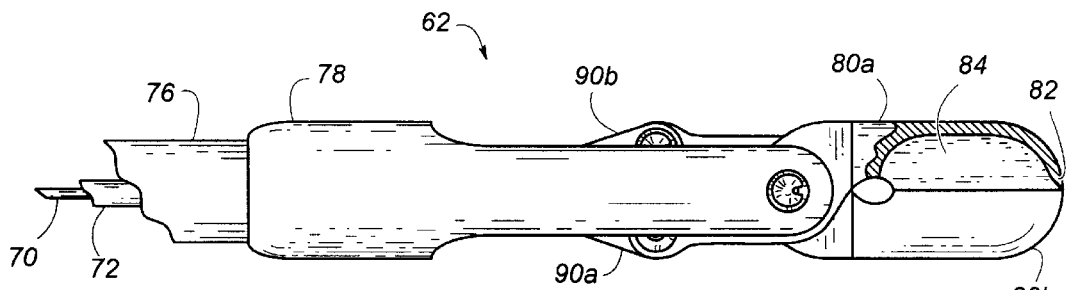
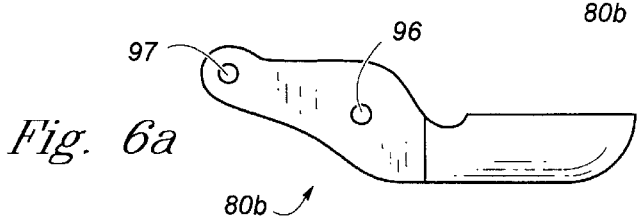
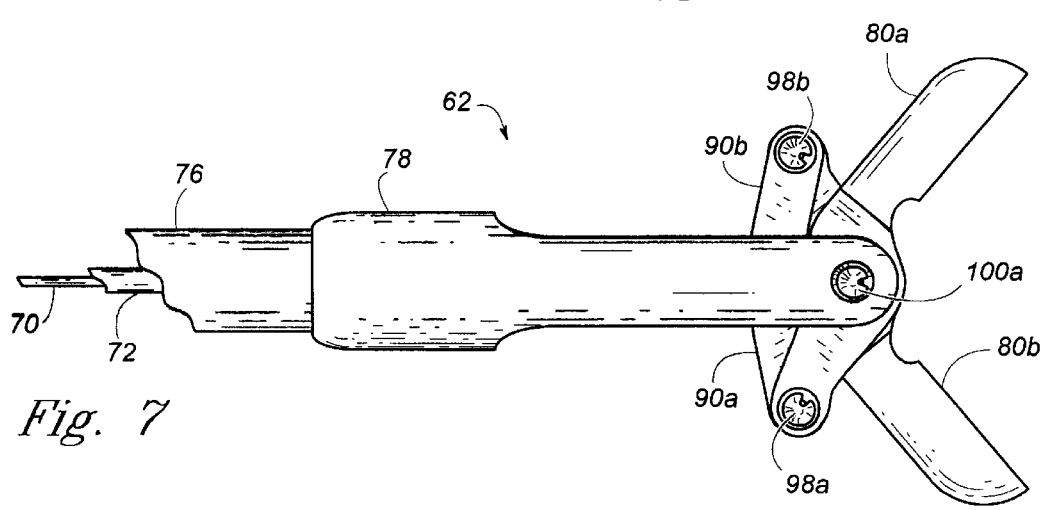

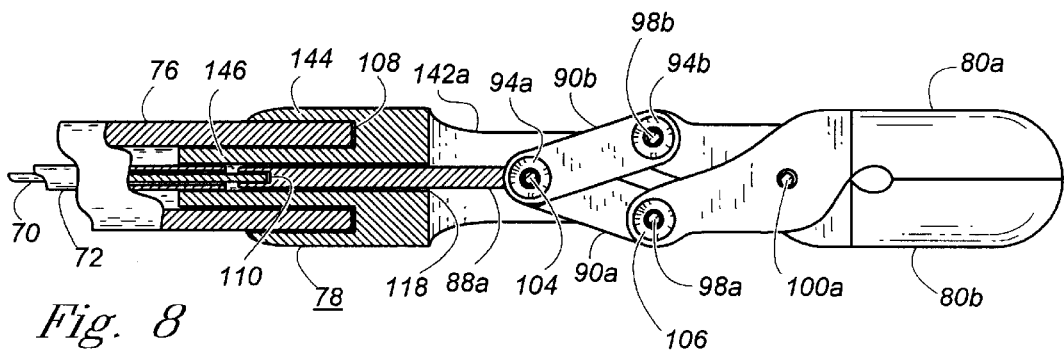
Fig. 8
Fig. 8a
Fig. 8b
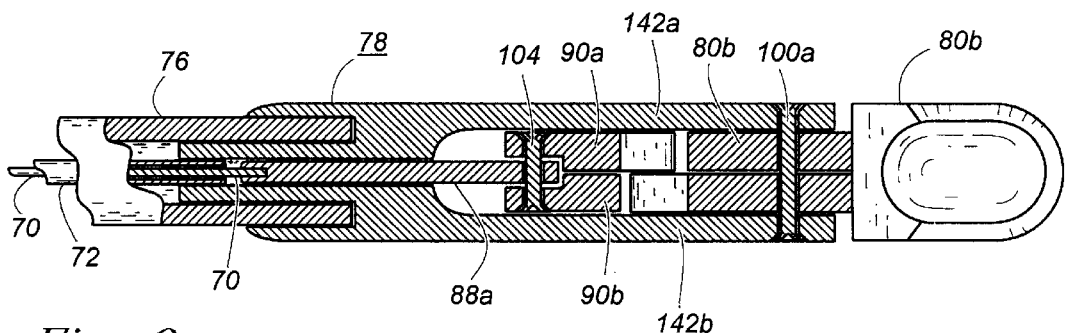
Fig. 9
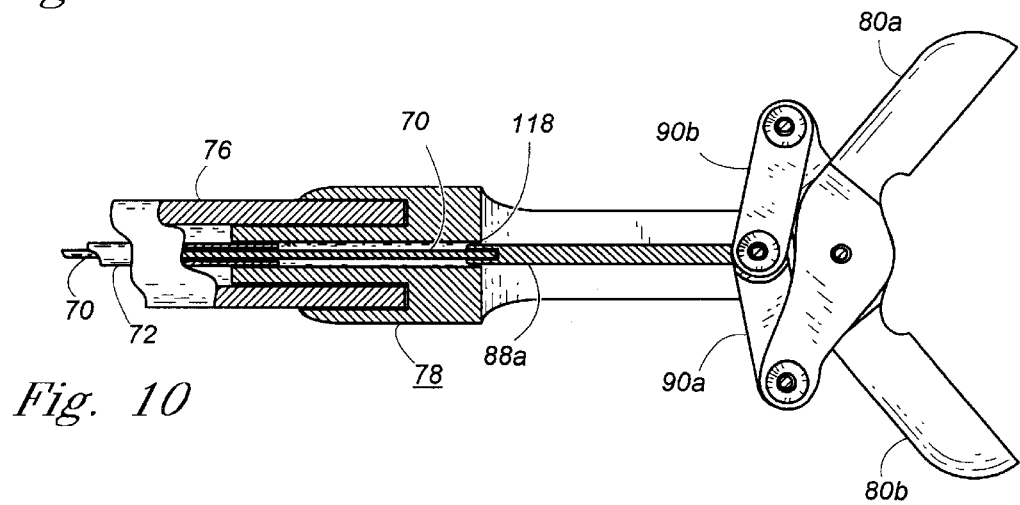
Fig. 10

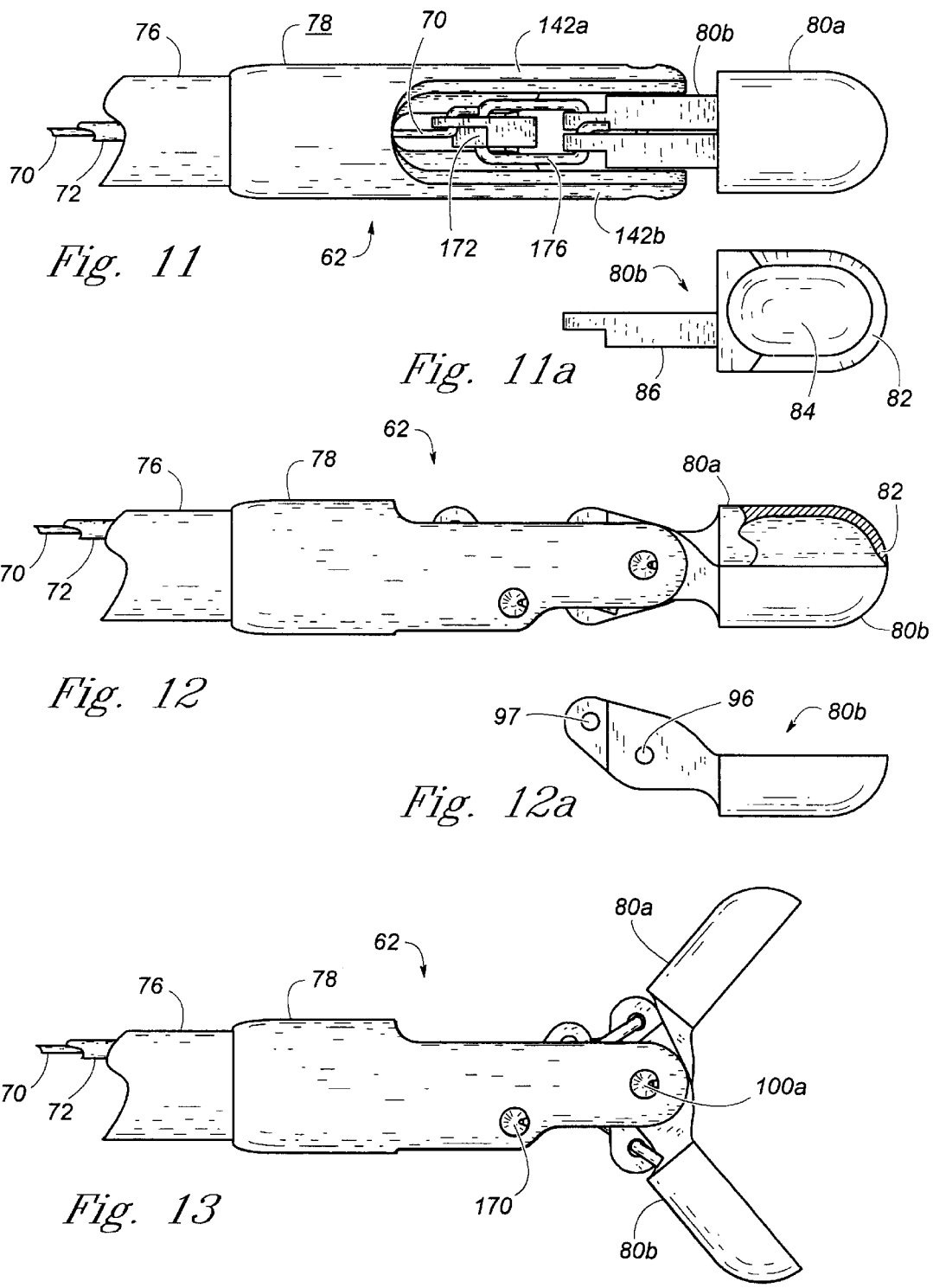

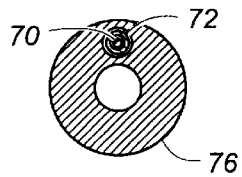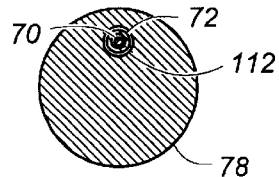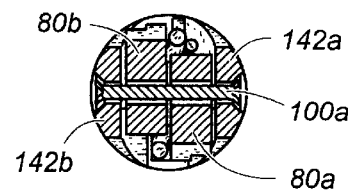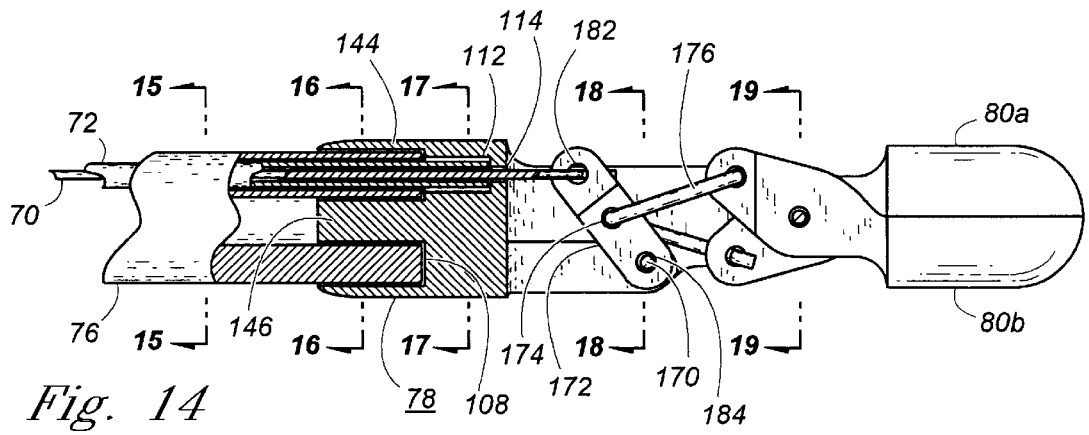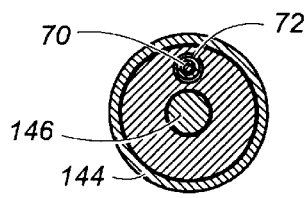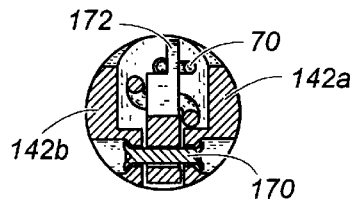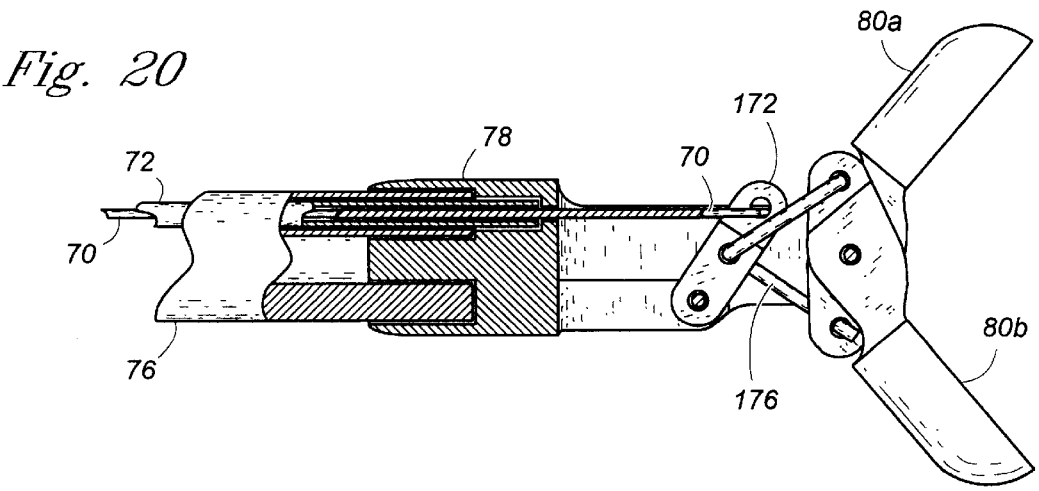

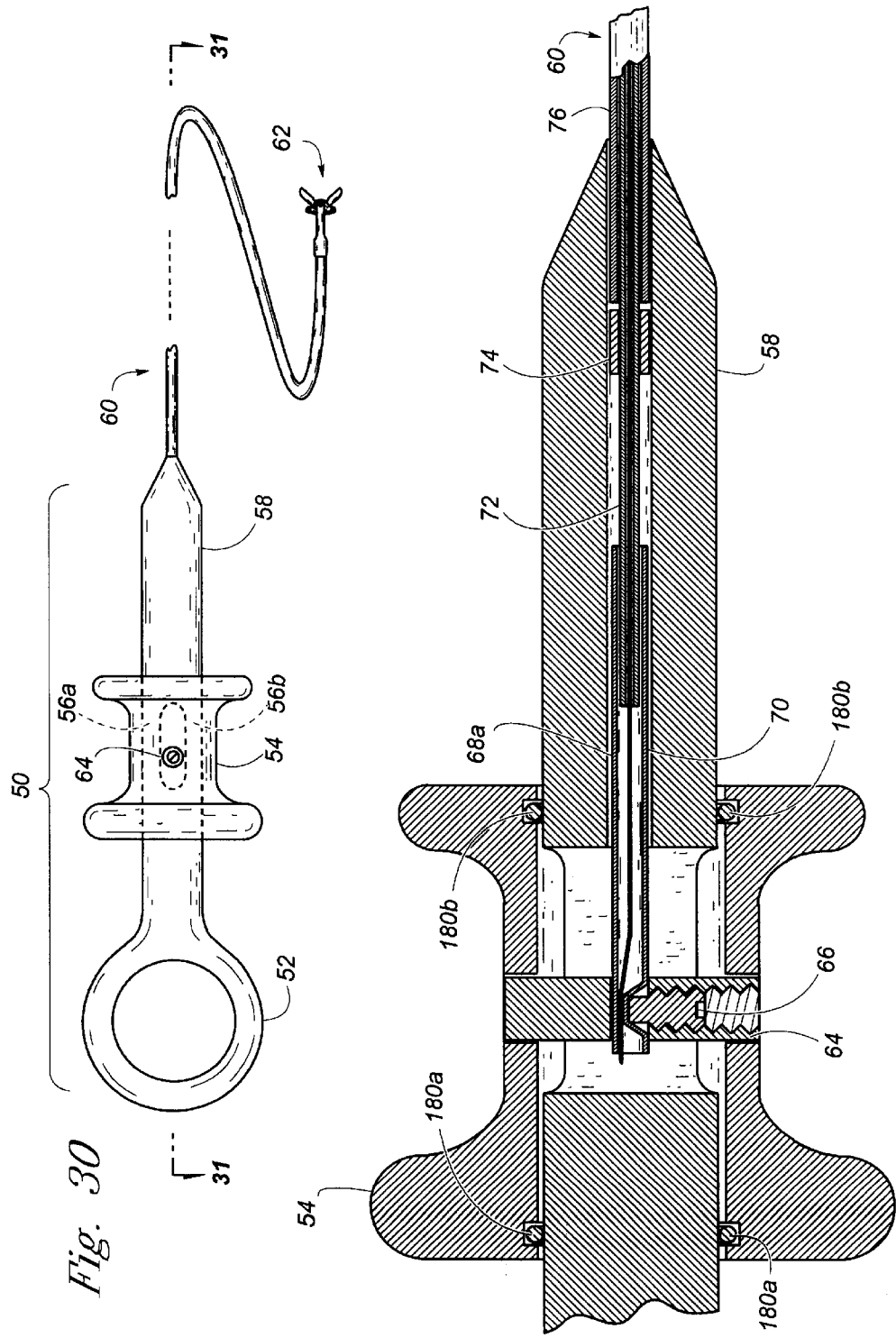

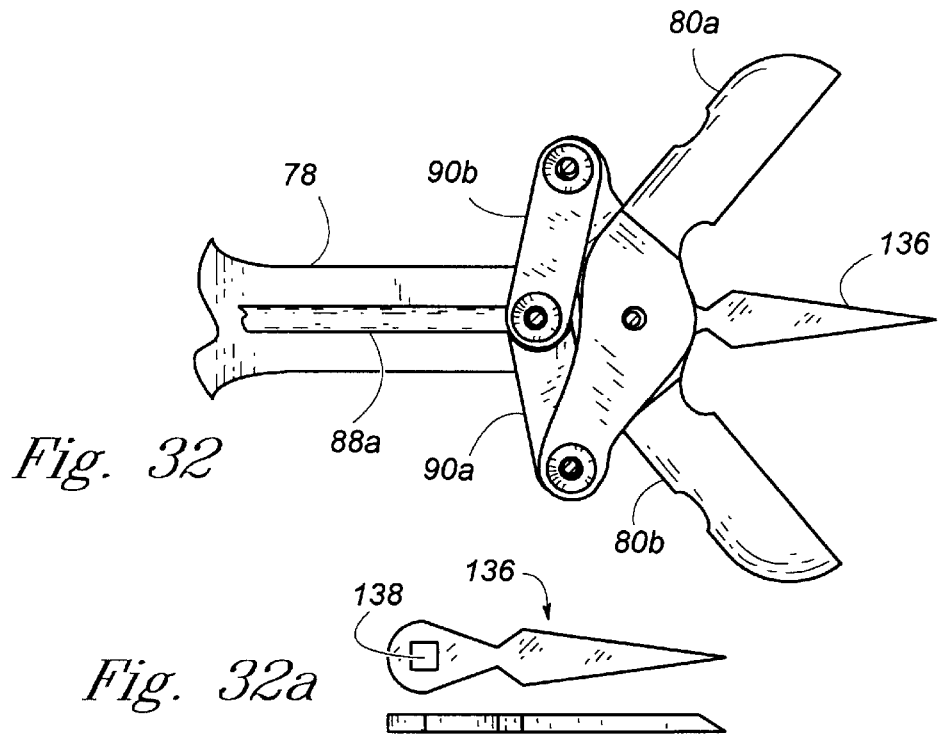
Fig. 32
Fig. 32a
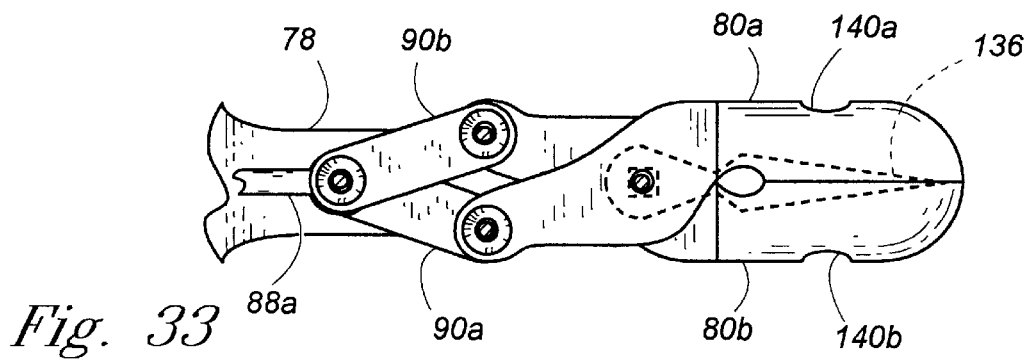
Fig. 33
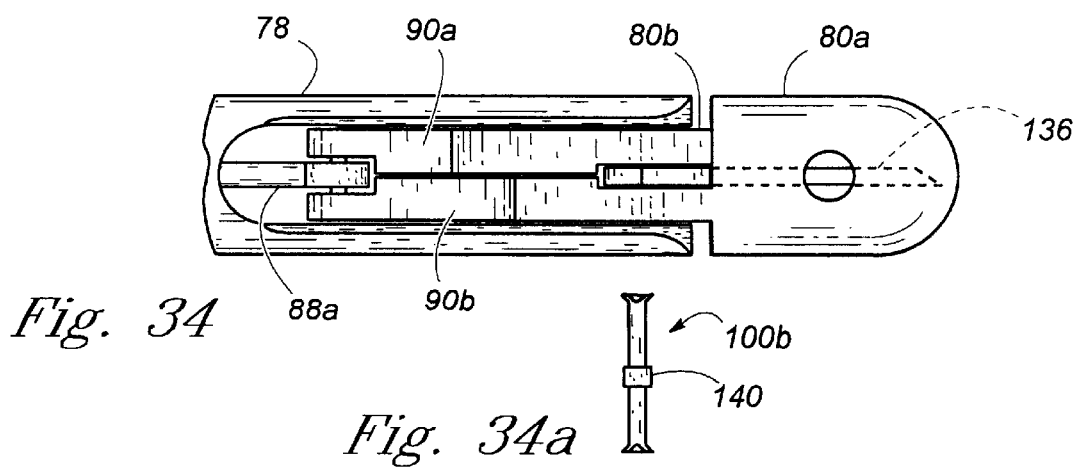
Fig. 34
Fig. 34a

FLEXIBLE FORCEPS DEVICE

BACKGROUND OF THE INVENTION

1. Field of the Invention

This invention relates to the field of medical instrumentation and more specifically to the field of endoscopic devices for grasping, cutting, removing or otherwise manipulating tissues and other materials inside a patient.

2. Description of the Prior Art

Devices for manipulating tissue are frequently used in minimally-invasive surgical and diagnostic procedures. Such procedures often involve the use of an endoscope, which allows visualization of inner structures of a patient without the need for conventional surgery. Manipulation of tissue is accomplished by passing specialized accessories through a hollow channel of the endoscope into the inner cavity of the patient, where the accessories perform functions such as cutting, grasping, snaring, dissecting, cauterizing and tissue sampling. The present invention relates to accessories used with endoscopes, as well as to accessories used without endoscopes, as in flexible biopsy forceps used for intravascular sampling of cardiac tissue. In particular, the present invention relates to flexible accessories such as forceps, that have movable elements located at the distal end.

Conventional forceps are comprised of an effector assembly at the distal end, a control assembly at the proximal end, and a tightly wound spring-coil extending between the distal and proximal ends. An actuating force is generated at the proximal end by a push-pull mechanism in the control assembly. This force is transferred to the distal end by pushing or pulling on one or more control wires extending through the lumen of the spring-coil to the effector assembly. The effector assembly is comprised of a support piece and one or more effectors. The effectors are fashioned for the specific function of the device, such as grasping, cutting or tissue sampling. Typically, the effectors are comprised of a pair of jaws that pivot about a fixed hinge-pin on the support piece. The control wire or wires are linked to the jaws, causing the jaws to open or close as a result of control wire pushing or pulling. Examples of such devices are disclosed in U.S. Pat. No. 4,178,810 (Takahashi) and U.S. Pat. No. 4,043,323 (Komiya).

Conventional forceps utilize the spring-coil body design because the spring-coil is very flexible, allowing it to conform to the tortuous path that may be encountered by a flexible endoscope. Typically, the body of a forceps device must be able to bend to a radius of one inch or less without permanently deforming. Further, the spring-coil enshrouds the control wire and protects it from kinking. Most importantly, the spring-coil is relatively incompressible along its long axis. Thus the spring-coil provides an effective column support between the control assembly and the effector assembly, allowing tensioning of the control wire without significant reduction in length of the spring-coil.

Despite these benefits, the spring-coil presents two problems to the user. First, although the spring-coil is relatively incompressible along its long axis, its bending stiffness can increase dramatically when the control wire is tensioned. As a result, tensioning of the control wire can cause a slight repositioning of the spring-coil within the channel of an endoscope as the spring-coil attempts to straighten itself. This repositioning can cause unwanted movement of the distal section, significantly interfering with accurate manipulation of the forceps during jaw closure. To address this problem, U.S. Pat. No. 5,228,451 (Bales) suggests covering the distal region of the spring coil with heat-shrinkable tubing. Unfortunately, the added layer increases the stiffness of the distal region, making the forceps body more difficult to insert into the endoscope channel, and making the distal portion of the endoscope more difficult to bend. Also, the heat-shrinkable tubing adds to the manufacturing cost of the device.

The second problem with the spring-coil body design involves cleaning. During a procedure, it is common for the spring-coil to become contaminated with patient fluids containing blood, mucous and feces. Using conventional cleaning procedures, it is difficult to remove all of the patient material from the crevices and inner surfaces of the spring-coil. This presents the potential for microbial and viral cross-contamination between sequential patients.

One solution to the cross-contamination problem is to make the device modular, as in U.S. Pat. No. 5,308,358 (Bond). Bond discloses a rigid surgical instrument wherein the body, control wire and effector assembly can be removed from the control assembly and individually cleaned. However, Bond does not offer a solution to the problem of cleaning the lumen and crevices of a flexible spring-coil. A modular version of a flexible forceps device is disclosed in U.S. Pat. No. 4,785,825 (Romaniuk), in which the flexible shaft, control assembly and effector assembly can be disassembled for adjustment and improved cleaning.

Another approach is to dispose of the entire device after a single use. In order for this approach to be economical, the cost of the device must be minimized. Low-cost designs have been suggested, as in U.S. Pat. No. 5,097,728 (Cox), U.S. Pat. No. 4,887,612 (Esser), and U.S. Pat. No. 5,133,727 (Bales). Cox discloses a low-cost stamped jaw design, Esser uses a simplified jaw mechanism and Bales describes a self-aligning, cast jaw assembly. While these designs show methods for reducing the cost of the jaw elements, they do not address cost reduction of the flexible forceps body.

U.S. Pat. Nos. 5,052,402 and 5,172,700 (both Bencini) suggest a plastic tube as a low-cost alternative to the conventional spring-coil, recommending polypropylene as an appropriate material. However, two key performance parameters need to be analyzed: 1) the change in length of the plastic tube as a function of the control wire force, and 2) the minimum bend radius attainable without permanent deformation. The change in length, $\Delta l$, of the tube can be estimated from the following equation: $\Delta l = LF/AE$, where L is the initial tube length, F is the control wire force, A is the cross-sectional area of the tube, and E is the elastic modulus of the material. As stated, a bend radius of about one inch or less is desirable for typical endoscopic applications. Assuming a bend radius of one inch, the maximum allowable tube diameter, d, can be estimated from the equation: $d=(2\sigma/E)r$, where E is the elastic modulus of the material, r is the bend radius, and $\sigma$ is the tensile strength of the material. For typical polypropylene, E=160,000 pounds per square inch (psi) and $\sigma$=5,000 psi, so the maximum outer tube diameter for a one-inch bend radius is: $d=(2/E)r=0.063$ inches. For a given outer tube diameter, the minimum change in tube length occurs when the cross-sectional area of the tube is maximized. Assuming a minimum control wire diameter of 0.007 inches and a minimum diametrical clearance of 0.001 inches, the minimum inner tube diameter would be 0.008 inches. With a typical endoscopic forceps body length of 94 inches, and a typical control wire actuating force of two pounds, the change in length of the plastic tube would be: l=0.38 inches. This change in length would result in a corresponding movement of the distal end of the forceps device of about 0.38 inches. Such movement would be large relative to the scale of endoscopic forceps—for example, typical biopsy forceps only open a maximum of 0.27 inches. Thus, movement of 0.38 inches would greatly interfere with the ability of the operator to accurately control the distal end of the forceps during jaw closure.

Other plastic materials would perform better than polypropylene for this application. For example, polyimide can have a modulus of elasticity of E=430,000 psi and a tensile strength of σ=25,000 psi. Using the equation for maximum outer diameter: d=(2σ/E)r=0.12 inches. However, in order to slide easily through a typical endoscope channel, the outer tube diameter must be constrained to about 0.080 inches. Using this outer tube diameter, and assuming an inner tube diameter of 0.008 inches, the change in length of a 94-inch polyimide tube under a two-pound load is: l=LF/AE=0.088 inches, which is less than the amount of movement observed with a conventional spring-coil forceps device. Unfortunately, polyimide tubing currently costs over ten times more than conventional spring-coils, making it an impractical choice for a low-cost forceps design.

A different solution to the cross-contamination problem is to make the accessory easier to clean. One method is disclosed in U.S. Pat. No. 4,646,751 (Maslanka), wherein the spring-coil is configured with a side port to allow the lumen to be flushed with cleaning fluid. Another method, as suggested in U.S. Pat. No. 3,964,468 (Schulz), is to cover the entire length of the spring-coil with a heat-shrinkable tubing and to seal the interfaces between the control wire and spring-coil lumen at both the proximal and distal ends. The disadvantage of Schulz is that the heat-shrinkable tubing reduces the flexibility of the spring-coil and adds to cost. In a similar embodiment disclosed in U.S. Pat. No. 5,035,248 (Zinnecker), the spring-coil is again covered with heat-shrinkable tubing and a silicone O-ring seal is disposed in the distal end between the control wire and lumen of the spring-coil. As in Schulz, the heat-shrinkable tubing reduces the flexibility of the spring-coil and adds to cost. Also, Zinnecker teaches no means for preventing contaminating fluids from entering the lumen of the spring-coil from the proximal end.

A better sealing approach is offered in U.S. Pat. No. 4,697,576 (Krauter), wherein a slidable cable for an endoscope is enshrouded by an elastomeric sealing sleeve which is anchored at one end and stretches as the cable slides back and forth. However, if such a seal was disposed at both the distal and proximal ends of the forceps body, the inner regions of the forceps body would be completely sealed, and thus air-tight. While creating an ideal seal from contaminants, it can cause a problem during certain disinfection procedures such as autoclaving wherein the temperature of the device is elevated and/or the device is exposed to increased pressures. In these situations, a completely sealed forceps body could be damaged by expansion or compression of the sealing members or tube walls. Thus, it is desirable to have a means for equalizing the pressure between the inner and outer regions of the forceps body. A similar problem exists with fully-sealed endoscopes—in U.S. Pat. No. 4,545,369 (Sato), an endoscope having a vent with a cap and filter is described. Similarly, U.S. Pat. No. 4,878,484 (Miyagi) discloses an endoscope vent with a heat sensitive valve.

Another problem frequently encountered with conventional flexible forceps devices involves the behavior of the movable elements in the effector assembly when the control assembly is released. Specifically, with most conventional flexible forceps designs, the operator must take care to keep the jaws in a closed position during insertion and withdrawal of the forceps through the channel of the endoscope. Otherwise, if the jaws inadvertently open, they can damage the walls of the endoscope channel. Also, if the forceps are used to retrieve tissue or materials from the inner regions of the patient, the sample may fall out of the jaws during the removal of the forceps unless the operator continuously keeps the jaws closed. Several solutions exist for this problem, including spring-return and locking-handle mechanisms such as disclosed in U.S. Pat. No. 4,815,476 (Clossick), U.S. Pat. No. 4,043,323 (Komiya) and U.S. Pat. No. 5,147,380 (Hernandez). However, such mechanisms generally aggravate the cleaning problem and increase cost.

There is, therefore, a need for a flexible forceps device having a body portion whose distal end does not significantly change position during movement of the control wire. There is also a need for a forceps device with means for keeping the movable elements in the effector assembly in a preferred orientation when the control assembly is released. There is a further need for a flexible forceps device that is easy to clean, can be disinfected using elevated temperatures, and is relatively inexpensive to produce.

SUMMARY OF THE INVENTION

In accordance with the present invention, there is provided a flexible forceps device comprised of a distal end to be inserted into a patient, a proximal end to remain outside the patient and a flexible, elongated body extending between the ends. The flexible body has at least one lumen and may have a smooth, sealed external surface. An effector assembly is attached to the distal end and includes a support piece and at least one movable element. A control assembly is attached to the proximal end and includes a push-pull mechanism. A coaxial actuating assembly extending through the lumen of the flexible body consists of a flexible tube having a lumen, with a control wire slidably disposed within the lumen of the tube. The tube provides a flexible, yet relatively incompressible column support between the effector assembly and control assembly. The proximal end of the control wire is attached to the push-pull mechanism and the distal end is linked to the movable elements, whereby operation of the control assembly moves the movable elements relative to the support piece. The coaxial actuating assembly undergoes a relatively small change in bending stiffness when the control wire is pushed or pulled, resulting in little displacement of the effector assembly relative to the control assembly during operation of the control assembly. Sealing means may be included to prevent fluids from contaminating the inner regions of the flexible body, and may be adapted to bias the movable elements to a preferred orientation. A vent may be included to allow disinfection at elevated temperatures and pressures.

In contrast with prior art devices, the flexible, elongated body of the present invention is not subjected to tension and compression along its long axis as a result of pushing and pulling on the control wire. Instead, these stresses are borne by the hollow tube portion of the coaxial actuating assembly. Thus, the body of the forceps device need not be incompressible along its long axis, and may therefore be extruded from low-cost, flexible plastic material with a smooth, easy-to-clean finish.

The hollow tube portion of the coaxial actuating assembly may be constructed from small-diameter, thin-wall stainless steel tubing. When properly fabricated, such tubing has the desired properties of flexibility in bending and incompressibility along its long axis. Drawn stainless steel tubing typically has an elastic modulus of about 29,000,000 psi and can have a tensile strength of 200,000 psi. Using the equations previously presented, the maximum tube diameter capable of a one-inch elastic bend radius is: $d=(2\sigma/E)r=0.014$ inches. By way of example, the hollow tube portion of the coaxial actuating assembly may have a diameter of 0.014 inches and a wall of 0.003 inches. The change in length of a 94-inch tube having these dimensions and undergoing a two-pound control wire force is: $\Delta l=LF/AE=0.063$ inches. Thus, the distal end of a forceps device constructed with such tubing would move relatively little during actuation of the control wire. Further, such tubing maintains a fairly constant bending stiffness when a control wire running through its lumen is tensioned. Other materials appropriate for the hollow tube include titanium and beryllium-copper. However, given current processing and material costs, the stainless steel approach is most economical.

Conventional stainless steel tubing is manufactured either by extrusion or by welding, followed by a drawing process. The welding process is generally more economical, especially if the tubing is welded to the desired final wall thickness without the need for extensive processing after welding. Conventional welding processes, such as Tungsten-Inert-Gas (TIG) welding, leave debris on the interior surfaces of the tubing, necessitating a deburring or plug-drawing operation which adds to cost. Laser welding, however, produces less debris inside the tubing, and can therefore be welded to the desired wall thickness and drawn to the desired outer diameter without the need for a plug-drawing step. Laser welding also results in a smaller heat-treated zone as compared to other welding processes, which results in relatively more bending flexibility. Thus, it is preferable that the hollow tube portion of the coaxial actuating assembly be made from laser-welded, thin-wall stainless steel tubing.

As previously described, the flexible, elongated body of the present invention can be constructed of a smooth-surfaced plastic extrusion—greatly simplifying the cleaning process relative to a conventional spring-coil body. The cleaning process is further simplified by the following improvements directed at preventing contaminating fluids from entering the lumen of the body and the lumen of the hollow tube portion of the actuator assembly. In one embodiment, the body is in sealing relationship with the effector assembly and with the control assembly, and sealing means are disposed near the distal end of the lumen of the forceps body. In another embodiment, sealing means are disposed near the proximal end of the lumen of the forceps body. In yet another embodiment, at least one of the sealing means is configured in such a way as to bias the movable elements to a preferred orientation when the control assembly is released.

It is among the general objects of the invention to provide a flexible forceps device that is easy to clean and disinfect using conventional methods.

Another object of the invention is to provide a flexible forceps device having a distal effector assembly with movable elements, such that the effector assembly undergoes little unwanted displacement relative to the control assembly during actuation of the movable elements.

A further object of the invention is to provide a flexible forceps device having a distal effector assembly with movable elements that are biased to a preferred orientation when the control assembly is released.

Another object of the invention is to provide a flexible forceps device that is relatively inexpensive to produce.

BRIEF DESCRIPTION OF THE DRAWINGS

The foregoing and other objects and advantages of the invention will be appreciated more fully from the following further description thereof, with reference to the accompanying drawings wherein:

FIG. 1 is a side view of a biopsy forceps device constructed in accordance with the present invention;

FIG. 2 is an enlarged, sectional top view of the control assembly of the embodiment illustrated in FIG. 1;

FIGS. 3 and 4 are sectional views through the control assembly illustrated in FIG. 2;

FIG. 5 is an enlarged top view of the effector assembly of the embodiment illustrated in FIG. 1, showing the jaws in their closed position;

FIG. 5a shows the lower jaw from the embodiment illustrated in FIG. 5;

FIG. 6 is a side view of the effector assembly of the embodiment illustrated in FIG. 5, showing a partial section of the upper jaw;

FIG. 6a is a side view of the lower jaw from the embodiment illustrated in FIG. 6;

FIG. 7 is a side view of the embodiment illustrated in FIGS. 5 and 6, showing the jaws in their fully open position;

FIG. 8 is a side view of the embodiment illustrated in FIGS. 5 and 6, with portions broken away to show details of the linkage mechanisms;

FIG. 8a is a perspective view of the pushrod from the embodiment illustrated in FIG. 8;

FIG. 8b is a side view of one of the two links from the embodiment illustrated in FIG. 8;

FIG. 9 is a sectional top view through the mid-line of the embodiment illustrated in FIG. 8, showing more details of the linkage mechanisms;

FIG. 10 is the same embodiment illustrated in FIG. 8, showing the jaws in their fully open position;

FIG. 11 is an enlarged top view of the effector assembly of a biopsy forceps device in accordance with a different embodiment of the invention, showing the jaws in their closed position;

FIG. 11a shows the lower jaw from the embodiment illustrated in FIG. 11;

FIG. 12 is a side view of the effector assembly of the embodiment illustrated in FIG. 11, showing a partial section of the upper jaw;

FIG. 12a is a side view of the lower jaw from the embodiment illustrated in FIG. 12;

FIG. 13 is a side view of the embodiment illustrated in FIG. 12, showing the jaws in their fully open position;

FIG. 14 is a side view of the embodiment illustrated in FIG. 12, with portions broken away to show details of the linkage mechanisms;

FIGS. 15 to 19 are various sectional views through the embodiment illustrated in FIG. 14;

FIG. 20 is the same embodiment illustrated in FIG. 14, showing the jaws in their fully open position;

FIG. 30 is a side view of a biopsy forceps device in accordance with a different embodiment of the invention, showing certain elements in phantom;

FIG. 31 is an enlarged, sectional top view of the control assembly of the embodiment illustrated in FIG. 30, showing molded packing elements therein;

FIG. 32 is an enlarged side view of the effector assembly of a biopsy forceps device in accordance with a different embodiment of the invention, with portions broken away to illustrate a needle element between the jaws, the jaws being in their fully open position;

FIG. 32a show side and edge views of the needle element illustrated in FIG. 32;

FIG. 33 is the same view illustrated in FIG. 32 with the jaws in their closed position, showing the needle element in phantom;

FIG. 34 is a top view of the embodiment illustrated in FIG. 33, showing the needle element in phantom;

FIG. 34a shows a top view of the jaw hinge pin from the embodiment illustrated in FIG. 34, with the hinge-pin having a shaped center section thereof.

DESCRIPTION OF THE PREFERRED EMBODIMENTS

Figure 21:
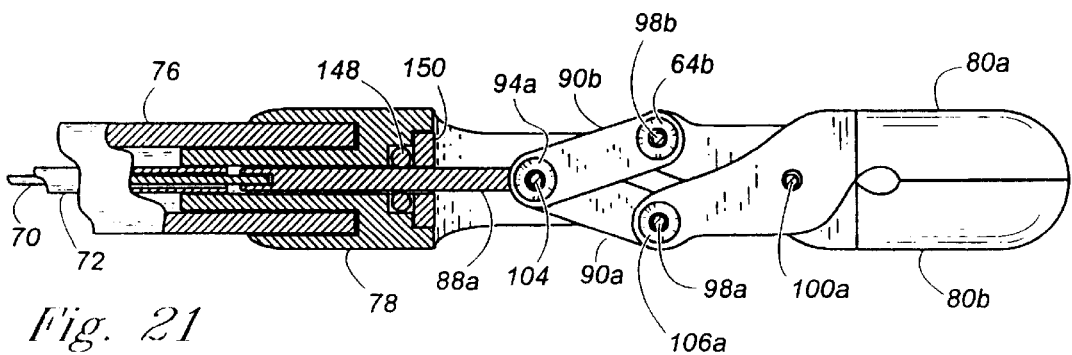
FIG. 21 is a modification of the embodiment illustrated in FIG. 8, incorporating a molded packing element therein.

FIG. 1 shows a flexible biopsy forceps device constructed in accordance with the present invention, consisting of an elongated, flexible body 60 having a control assembly 50 at its proximal end and an effector assembly 62 at its distal end. Flexible body 60 has at least one lumen extending therethrough and is formed preferably from a flexible, low-cost, extruded plastic material. Control assembly 50 is comprised of thumb ring 52 and finger spool 54, shaped so as to comfortably receive the thumb and fingers, respectively, of the operator. Finger spool 54 is slidably disposed on forked elements 56a and 56b, with cylindrical cross-bar 64 providing a guide means and travel limiting means for finger spool 54 along forked elements 56a and 56b. At the distal end of control assembly 50 is interface region 58, wherein flexible body 60 is anchored. Thumb ring 52, forked elements 56a and 56b and interface region 58 may be a single part molded from a plastic material such as ABS (acrylonitrile-butadiene-styrene).

FIG. 2 is an enlarged, sectional view of control assembly 50. Cross-bar 64, preferably fabricated from metal such as brass, has a blind, internally-threaded bore on one end to receive set screw 66. A transverse hole in the center of cross-bar 64 is located at the end of the threaded bore. Outer sleeve 68a enshrouds control wire 70 and is disposed into the transverse hole of cross-bar 64 such that advancement of set screw 66 will secure outer sleeve 68a and control wire 70 within the transverse hole. Outer sleeve 68a is preferably fabricated from metal tubing such as stainless steel, having an outer diameter on the order of 0.03 inches and a wall thickness of about 0.006 inches. As best seen in FIG. 3, a central bore through interface region 58 slidably receives the distal end of outer sleeve 68a, allowing free longitudinal movement of outer sleeve 68a within the bore, but relatively little lateral movement.

A coaxial actuating assembly is comprised of actuator tube 72 having a lumen through which control wire 70 extends. Control wire 70 is preferably made from high-strength stainless steel, and its diameter is chosen such that it will not break under the maximum reasonable tension exerted by the control assembly. By way of example only, control wire 70 may be fabricated from stainless steel wire having a tensile strength of 250,000 psi and a diameter of 0.007 inches, allowing up to 9.6 pounds of tensile force. Control wire 70 may also be made from stranded wire to improve flexibility, although it would need to be coated or impregnated or the like to allow it to undergo a compressive force without unraveling. The inner diameter of actuator tube 72 must be large enough to allow control wire 70 to slide easily therethrough. The outer diameter of actuator tube 72 is chosen to provide adequate bending flexibility, while the wall thickness is selected to provide enough axial strength. By way of example only, actuator tube 72 may have an outer diameter of 0.014 inches and a wall thickness of 0.003 inches and may be formed from stainless steel fabricated using a laser-welding process.

Actuator tube 72 is attached to cylindrical proximal anchor 74 using a method such as brazing, soldering or adhesive bonding. Proximal anchor 74, which may be a section of metal tubing, is attached to the bore of interface region 58 by press-fitting, adhesive bonding or the like. It will be appreciated that proximal anchor 74 may be eliminated by incorporating an analogous anchoring region for actuator tube 72 directly into interface region 58. Actuator tube 72 extends beyond proximal anchor 74 to be slidably received by the lumen of outer sleeve 68a. The length of outer sleeve 68a is chosen such that at the proximal-most position of finger spool 54, actuator tube 72 remains within the lumen of outer sleeve 68a. Likewise, at the distal-most position of finger spool 54, anchor 74 is positioned so as not to impede distal movement of outer sleeve 68a. Thus, control wire 70 is fully constrained radially by the combination of outer sleeve 68a and actuator tube 72, in such a way as to allow compressive forces to be applied to control wire 70 without causing deformative buckling. With this arrangement, pulling or pushing on finger spool 54 relative to thumb ring 52 is translated into pulling and pushing motion, respectively, of control wire 70 relative to actuator tube 72.

The proximal end of elongated, flexible body 60 is fixedly disposed within the distal end of the central bore of interface region 58, using adhesive bonding or the like. Flexible body 60 is comprised of flexible tube 76 having a lumen extending therethrough. As can be seen in FIG. 4, the coaxial actuator assembly, consisting of actuator tube 72 and control wire 70, extends through the lumen of flexible tube 76. The properties of flexible tube 76 are chosen so as to give flexible body 60 the proper stiffness, kink-resistance and resiliency. It will be appreciated that these properties may be altered not only by material selection and tube geometry, but by stiffening wires, braided layers and the like added to or incorporated within flexible tube 76. Flexible tube 76 preferably has a relatively lubricous surface so as to ease the process of inserting the device through the channel of an endoscope. As an example, flexible tube 76 may be extruded from a fluoropolymer or fluoroelastomer. Alternatively, flexible tube 76 may be extruded from a less-expensive polymer such as PVC (polyvinyl chloride) and subjected to a surface modification or coating process to improve lubricity. Surface modifications to improve lubricity include gas plasma treatment (Polar Materials/Wheaton, Inc., Pennsville, N.J.) and ion beam deposition (Spire Corporation, Bedford, Mass.). Lubricous coatings include parylene (Advanced Surface Technology, Inc., Billerica, Mass.), fluoropolymer (Advance Coating Technology, Mechanicsburg, Pa.) and various hydrogels (BSI Corporation, Eden Prairie, Minn.). The outer diameter and length of flexible body 60 are dictated by the constraints of the endoscope for which the forceps are intended. Most accessories for flexible endoscopes typically have outer diameters from 0.02 to 0.12 inches and lengths from 30 to 100 inches. The inner diameter of flexible tube 76 must be large enough to accommodate actuator tube 72. By way of example only, flexible tube 76 may have an outer diameter of 0.08 inches, an inner diameter of 0.040 inches and a length of 94 inches.

FIG. 5 shows a top view of the effector assembly of a biopsy forceps device constructed in accordance with the present invention. Biopsy forceps are used in endoscopic procedures for removing and recovering samples of tissue from inner regions of the body of a patient. Biopsy forceps generally have a pair of cupped jaws that pivot from an open position to a closed position, in response to movement of the control wire. Typically, pulling on the control wire closes the jaws, capturing tissue within the cups. The forceps device is then removed from the endoscope and the tissue sample is taken from the jaws for further analysis. While biopsy forceps may be an appropriate application of the present invention, it should be kept in mind that any endoscopic accessory with at least one moving effector in the distal region may be constructed using the principles of the present invention. Examples of other appropriate devices include grasping forceps, dissectors, retrieval forceps and cutting forceps. Additionally, the present invention may be applied to accessories used with industrial borescopes.

It will be appreciated that minimization of friction between control wire 70 and actuator tube 72 will likewise maximize the amount of force available at effector assembly 62 for a given force applied at control assembly 50. While the coefficient of friction between stainless steel wire and stainless steel tubing is relatively low, means may be incorporated within the coaxial actuator assembly to further reduce friction. For example, a lubricous coating or surface treatment may be applied to at least one of the outer surface of control wire 70 or inner surface of actuator tube 72. Alternatively, a lubricant or a sleeve having lubricous properties may be disposed between control wire 70 and actuator tube 72.

In FIG. 5, the distal ends of flexible tube 76, actuator tube 72 and control wire 70 are shown interfacing to effector assembly 62. Effector assembly 62 consists of pushrod 88a, links 90a and 90b, jaws 80a and 80b, jaw support 78 and various hinge-pins. Jaws 80a and 80b are shown in their fully closed position. FIG. 5A illustrates lower jaw 80b, showing jaw cup 84, cutting edge 82 and lever arm 86. In the embodiments illustrated throughout this disclosure, jaws 80a and 80b are identical, although this need not be a design constraint. FIG. 6 shows a side view of the effector assembly depicted in FIG. 5, with a partial section of jaw 80a illustrating the arrangement of jaw cup 84 and cutting edge 82. Also shown are links 90a and 90b. FIG. 6A is a side view of jaw 80b, showing lever hole 97 and pivot hole 96. FIG. 7 shows the same view as FIG. 6, with control wire 70 having been pushed in a distal direction, causing links 90a and 90b to pivot, thereby opening jaws 80a and 80b. Riveted hinge-pins 98a and 98b pivotally join links 90a and 90b to jaws 80a and 80b, respectively. Riveted hinge-pin 100a pivotally joins jaws 80a and 80b to jaw support 78.

FIGS. 8 and 9 show detailed views of the embodiment depicted in FIG. 6, with portions broken away to reveal the inner mechanisms. Jaw support 78 is comprised of an outer cylindrical section 144, inner cylindrical section 146 with central bore 118 extending therethrough, annular groove 108, and a pair of prongs 142a and 142b. The opposing inner surfaces of prongs 142a and 142b are flat and parallel to each other. Flexible tube 76 is captured in annular groove 108 and affixed therein by a resilient adhesive such as silicone or polyurethane to ensure a water-tight seal between flexible tube 76 and jaw support 78. The outer surface of the distal end of actuator tube 72 is attached to the inner surface of the proximal end of central bore 118 by means of soldering, brazing, welding, adhesive bonding or the like. Control wire 70 is slidably disposed within the lumen of actuator tube 72. The distal end of control wire 70 extends through central bore 118 and is fixedly disposed in blind hole 110 in the proximal end of pushrod 88a by means of crimping, soldering, brazing, welding, adhesive bonding or the like. As shown in FIG. 8A, the distal end of pushrod 88a is comprised of pivot ring 120 having pivot hole 122 therethrough, with pivot ring 120 having flat, parallel sides. Pushrod 88a is captured between links 90a and 90b, with riveted hinge-pin 104 pivotally joining the three elements, as shown in FIG. 9. FIG. 8B shows the inner face of link 90a, having a pair of holes 152a and 152b, with hole 152a being surrounded by recessed area 92 fashioned to capture pivot ring 120. As can be seen in FIG. 8, the outer face of link 90b has a pair of countersunk regions 94a and 94b concentric with holes 152a and 152b shown in FIG. 8B. While links 90a and 90b are identical in the embodiments presented, this need not be a design constraint. Link 90b is joined to jaw 80b by riveted hinge-pin 98b. Jaws 80a and 80b are joined to jaw support 78 by riveted hinge-pin 100a.

FIG. 10 shows the same view of the embodiment illustrated in FIG. 8, with control wire 70 pushed to its distal-most position such that jaws 80a and 80b are in their fully open position. The length of pushrod 88a is chosen such that in its distal-most position, the proximal end will remain within central bore 118 of jaw support 78. Otherwise, if pushrod 88a is allowed to slip out of central bore 118, pushing on control wire 70 may result in unwanted pivoting of jaws 80a and 80b about hinge-pin 100a.

Jaw support 78, jaws 80a and 80b, and pushrod 88a are substantially intricate parts which are subjected to high stresses. Therefore, the preferred material for these parts is relatively hard metal such as stainless steel. These parts may be fabricated by any of the conventional methods such as machining, metal injection molding, investment casting, powder metallurgy or some combination thereof. Links 90a and 90b may also be fabricated from relatively hard metal and may be formed by a stamping process.

FIGS. 11 through 20 show views of the effector assembly of a different biopsy forceps device constructed in accordance with the present invention. In this embodiment, the coaxial actuator assembly is offset from the central axis of flexible tube 76. FIG. 11 shows a top view of effector assembly 62, with FIG. 11A showing details of lower jaw 80a. FIG. 12 is a side view of the effector assembly from FIG. 11, and FIG. 12A shows a side detail of lower jaw 80b. FIG. 13 shows the embodiment from FIG. 12 with control wire 70 pushed distally to fully open jaws 80a and 80b.

FIG. 14 illustrates the effector assembly from FIG. 12 with portions broken away to reveal details of the inner mechanisms. FIGS. 15 through 19 illustrate sections through the effector assembly shown in FIG. 14. Actuator tube 72 and control wire 70 extend through a secondary lumen in flexible tube 76 which is offset from the central axis of flexible tube 76. Flexible tube 76 is captured in annular groove 108 and affixed therein by a resilient adhesive such as silicone or polyurethane to ensure a water-tight seal between flexible tube 76 and jaw support 78. The hollow central lumen of flexible tube 76 may be adapted to provide fluid functions such as air, water or suction, or it may be adapted to provide optical or electrical functions or the like. Alternatively, flexible tube 76 may not have a hollow central lumen and jaw support 78 likewise may have no inner cylindrical section 146. The distal end of actuator tube 72 is attached to bore 112 by means of soldering, brazing, welding, adhesive bonding or the like. Control wire 70 is slidably disposed within the lumen of actuator tube 72 and extends distally through hole 114 to engage hole 182 of lever link 172. Riveted hinge-pin 170 passes through pivot hole 184, pivotally joining lever link 172 to prongs 142a and 142b, as best seen in FIG. 18. V-shaped connecting wire 176 passes through hole 174 of lever link 172 and engages each pivot hole 97 of jaws 80a and 80b. Jaws 80a and 80b are pivotally captured between prongs 142a and 142b by means of riveted hinge-pin 100a, as seen in FIG. 19. With this configuration, pulling or pushing on control wire 70 relative to actuator tube 72 causes lever link 172 to pivot around hinge-pin 170, such pivoting causing connecting wire 176 to move proximally or distally, respectively, which causes jaws 80a and 80b to close or open, respectively. FIG. 20 shows the effector assembly depicted in FIG. 14 with control wire 70 pushed distally to fully open jaws 80a and 80b. Connecting wire 176 may be formed from an appropriate material such as high-strength stainless steel or beryllium-copper. Alternatively, connecting wire 176 may be divided into two separate links, in which case another hole would need to be added to lever link 172.

There are at least three advantages of the embodiment of FIG. 14 relative to that disclosed in FIG. 8. First, effector assembly 62 is shorter in the embodiment of FIG. 14. A shorter effector assembly makes the forceps easier to insert through the narrow, bending channel of a flexible endoscope. Effector assembly 62 in FIG. 14 is shorter than that in FIG. 8 primarily because lever arms 86 of jaws 80a and 80b are shorter in the embodiment of FIG. 14. Shorter lever arms 86 are possible because lever link 172 serves to double the force translated from control wire 70 to lever holes 97 of jaws 80a and 80b. Thus, for a given force on control wire 70, the jaw opening or closing force will be roughly the same in both embodiments. The second advantage of the current embodiment is that effector assembly 62 has fewer parts than the embodiment of FIG. 8: pushrod 88a, links 90a and 90b, hinge-pins 98a, 98b and 104 have been replaced with lever link 172, connecting wire 176 and hinge-pin 170. Pushrod 88a is unnecessary in the embodiment of FIG. 14 because there is no chance of unwanted rotation of jaws 80a and 80b around hinge-pin 100a. The third advantage is that connecting wire 176 may be formed such that its relaxed shape is as shown in FIG. 14, thereby serving as a spring-return to keep jaws 80a and 80b in their closed position when control assembly 50 is released.

FIG. 21 shows the effector assembly of a biopsy forceps device similar to that depicted in FIG. 8, but having an improved sealing feature. In this embodiment, molded packing 148 and retaining ring 150 have been added to a circular recess in jaw support 78. Molded packing 148 is sized to fit snugly in its recess and to tightly squeeze pushrod 88a. Molded packing 148 is fabricated preferably from a resilient material such as silicone that can withstand steam autoclaving and exposure to strong disinfecting agents. Retaining ring 150 has a central hole that allows pushrod 88a to slidably pass therethrough without binding. Retaining ring 150 is affixed to jaw support 78 by adhesive bonding or the like so as to trap molded packing 148 in its recess.

It will be appreciated that the combination of molded packing 148 and the seal formed between flexible tube 76 and jaw support 78 will prevent contaminating fluids at the distal end of the forceps device from reaching the lumen of flexible tube 76 and actuator tube 72. Thus, the only distal surfaces of the forceps device that may be exposed to contaminating fluids are the outer surface of flexible tube 76 and the surfaces of effector assembly 62. This confinement of contamination greatly simplifies the cleaning process relative to prior art devices having spring-coil bodies whose crevices and lumina need to be cleaned.

Molded packing 148 is shown in the form of an O-ring in FIG. 21. However, an O-ring is only one example of a molded packing which may be used for the indicated sealing purpose. Other types of molded packings may also be used, such as D-rings, T-rings, U-rings, V-rings, delta-rings, lobed-rings, rod wipers and the like. Molded packings generally rely on a pressure difference across the packing to help create an effective seal. Since there is no pressure difference in this case, sealing efficacy is limited by the amount of squeezing force that can be applied by the molded packing against pushrod 88a. This squeezing force can be enhanced by compressive pressure from retaining ring 150 against the molded packing. Sealing efficacy is also affected by the surface finish of pushrod 88a and the roundness of the cross-section of pushrod 88a—a better seal is obtained with a smoother finish and a rounder cross-section. Unfortunately, pushrod 88a is a fairly small, complicated part, and to produce it at low cost with a consistently smooth finish and a round cross-section is challenging.

Figure 22:
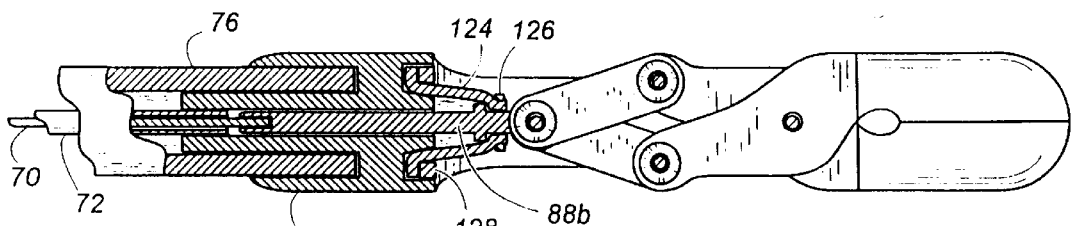
FIG. 22 is a modification of the embodiment illustrated in FIG. 8, incorporating a sealing boot therein.
Figure 22A:
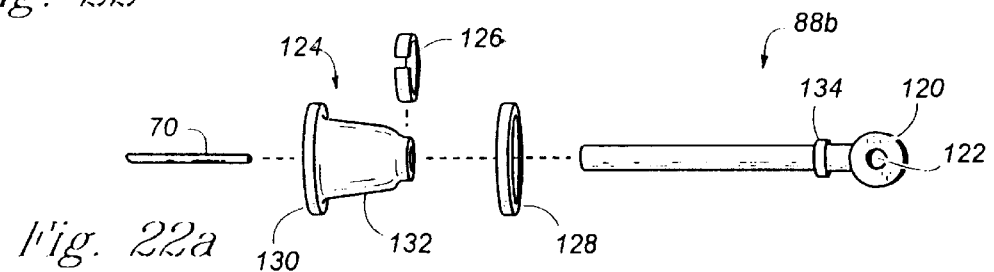
FIG. 22a is an exploded, perspective view of the sealing elements relating to the embodiment illustrated in FIG. 22.

FIG. 22 shows a side sectional view of the distal region of a different embodiment of a biopsy forceps device having a sealing feature designed to overcome the shortcomings of the molded packing approach. A sealing boot 124 is disposed between jaw support 78 and the distal end of pushrod 88b. FIG. 22A is an exploded view showing the relationship between the sealing elements. Sealing boot 124 has proximal flange 130 and expansion section 132. Pushrod 88b is equivalent to previously-described pushrod 88a, with the addition of raised rib 134 near its distal end. Flange 130 of sealing boot 124 is disposed in a recess of jaw support 78 and captured by retaining ring 128 which is adhesively bonded to jaw support 78. The distal end of sealing boot 124 is squeezed tightly by collar 126 above raised rib 134 on pushrod 88b, so as to create a water-tight seal. A sealing agent such as silicone or polyurethane may be used to further enhance the water-tight seal. In the embodiment shown, sealing boot 124 may be formed from an elastomeric material which can easily stretch to several times its relaxed length. In addition, the material chosen for sealing boot 124 must be able to withstand disinfection processes such as steam autoclaving and immersion in liquid chemical germicides. As an example, sealing boot 124 may be molded from a silicone elastomer such as MED-4735, available from Nusil Technology (Carpinteria, Calif.). This material has an elastic modulus of 150 psi and a tensile strength of 1310 psi.

Figure 23:
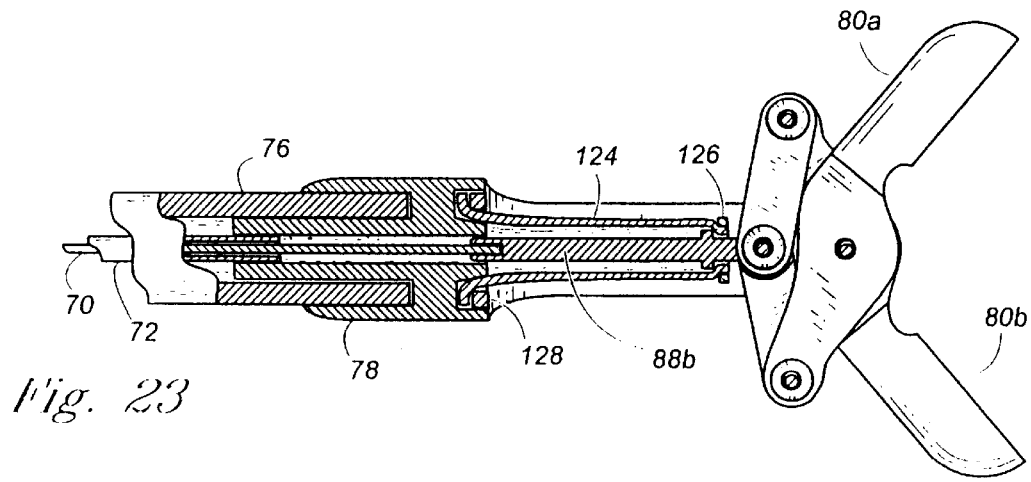
FIG. 23 is the same view illustrated in FIG. 22, with the jaws in their fully open position.

FIG. 23 shows sealing boot 124 fully stretched when control wire 70 is pushed to its distal-most position so as to open jaws 80a and 80b. In the embodiment shown, expansion section 132 of sealing boot 124 elongates by 275%. By way of example only, sealing boot 124 may have a relaxed length of 0.06 inches, an outer diameter of 0.045 inches and a wall thickness of 0.008 inches.

It will be appreciated that the combination of sealing boot 124 and the seal formed by flexible tube 76 and jaw support 78 will prevent contaminating fluids at the distal end of the forceps device from reaching the lumen of flexible tube 76 or actuator tube 72. The sealing boot approach represents an improvement over the molded packing approach in that the surface finish and cross-section of pushrod 88b are much less critical, making pushrod 88a more economical to manufacture.

A further advantage of the embodiment illustrated in FIGS. 22 and 23 is that sealing boot 124 acts to keep jaws 80a and 80b in their closed position in the absence of a pushing force on control wire 70. As described previously, this may be desirable for purposes of protecting endoscope channels and for retaining retrieved samples within the jaws.

Alternate configurations of sealing boot 124 can impart different traits to the forceps device. For example, if sealing boot 124 is formed such that its relaxed position is the longer length shown in FIG. 23, then a force would be required to compress the boot as the jaws are closed. Alternatively, if sealing boot 124 is formed with convoluted folds, as in a bellows, then there would be no favored position and little additional force would be required to transition from the open-jaw position to closed-jaw position and back. Such a bellows could be molded from an elastomeric material, or it could be electroformed from metal by a manufacturer such as Servometer Corporation (Cedar Grove, N.J.). An additional option is to make sealing boot 124 a rolling-type diaphragm molded from fabric-reinforced elastomeric material. Such a rolling-type diaphragm would be shaped similarly to sealing boot 124, but instead of stretching and contracting, it would unfold and fold into itself. Custom-made rolling-diaphragms are available from Diacom Corporation (Amherst, N.H.).

Figure 24:
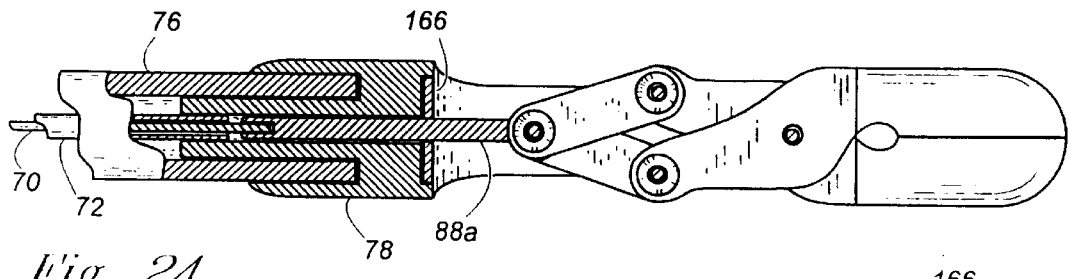
FIG. 24 is a modification of the embodiment illustrated in FIG. 8, incorporating a diaphragm element therein.
Figure 24A:
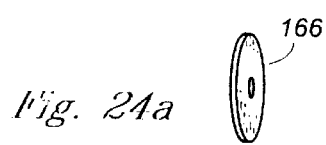
FIG. 24a is a perspective view of the diaphragm element from the embodiment shown in FIG. 24.
Figure 24B:
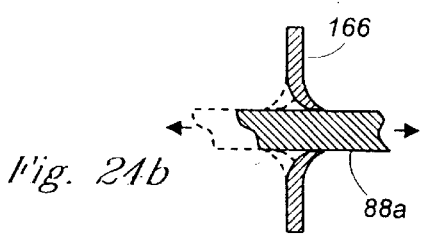
FIG. 24b is an enlarged sectional view illustrating the interface between the diaphragm element and the pushrod element from FIG. 24, showing two different positions, one being in phantom.

Both the molded packing approach and sealing boot approach require delicate assembly of relatively small parts, potentially adding to the overall cost of the device. FIG. 24 illustrates a simpler alternative to the molded packing and sealing boot approaches. Flat diaphragm 166, having a central hole with a diameter slightly smaller than the diameter of pushrod 88a, is bonded directly to a circular recess in jaw support 78. FIG. 24A shows a perspective view of diaphragm 166, while FIG. 24B shows a section view through the center of diaphragm 166 and pushrod 88a. In FIG. 24B, pushrod 88a is shown in a distally-sliding position and, in phantom, in a proximally-sliding position. The lip of the central hole through diaphragm 166 tightly surrounds and wipes pushrod 88a as it slides through the hole, thereby preventing contaminants from entering the inner regions of flexible body 60. Diaphragm 166 is preferably fabricated from an elastomeric material such as silicone. Alternatively, diaphragm 166 may be fabricated from a microporous membrane material made from woven nylon or polyester or the like. Such membrane material may have hydrophobic properties and is available from Performance Systematix, Inc. (Caledonia, Mich.).

Figure 25:
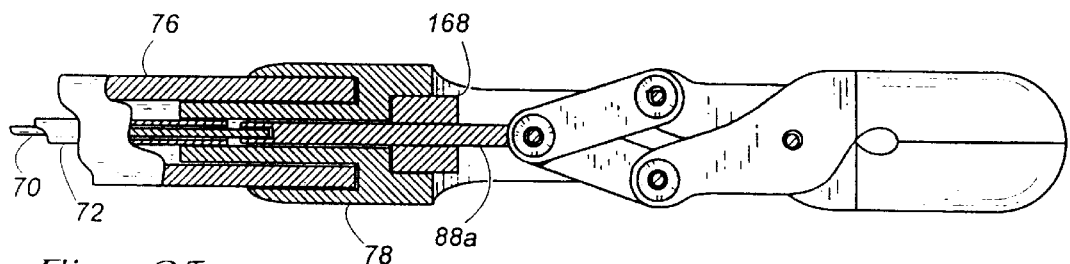
FIGS. 25 and 25a show a modification of the embodiment illustrated in FIG. 8, incorporating a plug element therein.
Figure 25A:
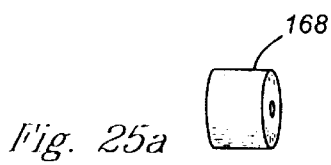

Another simple sealing alternative is shown in FIG. 25, wherein cylindrical plug 168 made of a closed-cell foam or hydrophobic material is bonded to jaw support 78. Plug 168, shown in perspective in FIG. 25A, has a central hole for tightly receiving pushrod 88a. Examples of appropriate closed-cell foam materials include EPT foam (ethylene propylene terpolymer), available from Rubatex Corporation (Bedford, Va.) and silicone foam, available from Lauren Manufacturing Co. (New Philadelphia, Ohio) and others. Since such materials may absorb small amounts of liquid, an anti-microbial agent may be added to the foam to prevent microbial growth. Hydrophobic materials, such as those made from fluoropolymer and PPC (polyphthalate carbonate), are available from Porex Technologies Corporation (Fairburn, Ga.) and others.

Figure 26:
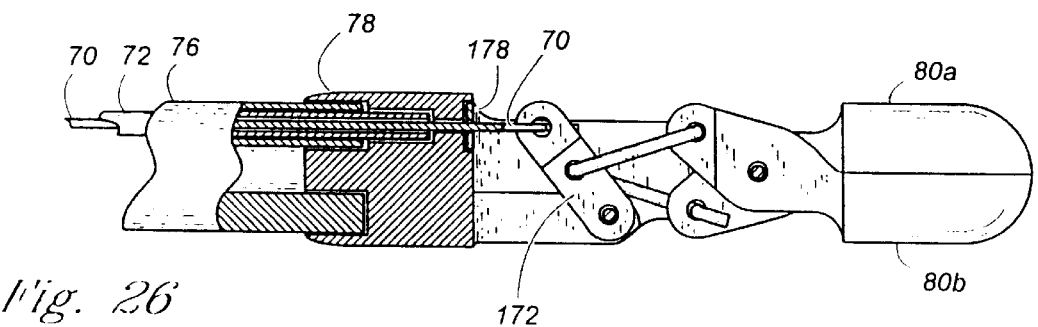
FIG. 26 is a modification of the embodiment illustrated in FIG. 14, incorporating a diaphragm element therein.

The embodiments disclosed in FIGS. 21 through 25 show distal sealing means for effector assemblies similar to that depicted in FIG. 8. It will be appreciated that each of the sealing means illustrated may also be applied to the effector assembly disclosed in FIG. 14. As an example, FIG. 26 shows the effector assembly from FIG. 14 incorporating elastomeric diaphragm 178 similar to that shown in FIG. 24.

The prior embodiments address sealing of the distal region of the forceps device. However, it is common during conventional cleaning procedures for the entire forceps device to be submerged in cleaning or disinfecting solutions, making it possible for fluids to infiltrate the lumen of flexible body 60 body from the proximal end. Although such fluids may have much lower levels of contamination than those encountered at the distal end, any standing fluid left inside the lumen potentially becomes a site for microbial growth. Such microbial growth could make its way out of the lumen during a subsequent use of the device, endangering the operator and indirectly endangering the patient. Thus, it would be beneficial to provide a sealing means at the proximal end to preclude this contamination path. Referring to FIG. 2, the contamination paths are primarily through the proximal opening of outer sleeve 68a and through the annular space between outer sleeve 68a and interface section 58. It is assumed that the bond between flexible body 76 and interface section 58 provides a water-tight seal, as can be achieved with conventional bonding agents such as silicone and polyurethane.

Figure 27:
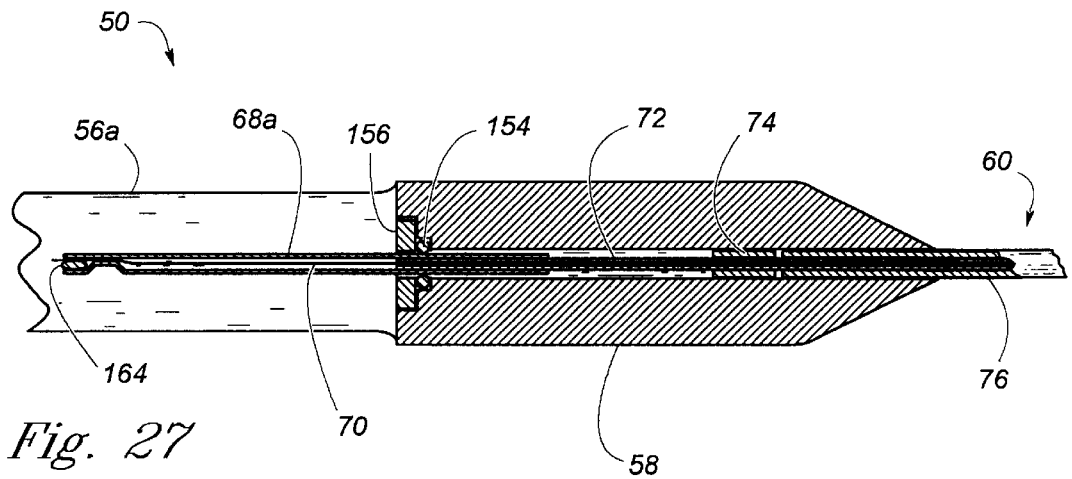
FIG. 27 is a modification of the control assembly illustrated in FIG. 2, incorporating a molded packing element therein.

FIG. 27 shows a sectional side view of a portion of the control assembly from the embodiment illustrated in FIG. 2. Finger spool 54, cross-bar 64 and set screw 66 have been omitted from the drawing for clarity. Molded packing 154 has been added to interface section 58, sized to tightly squeeze outer sleeve 68a. Molded packing 154 is held tightly in its recess by retaining ring 156, which may be adhesively bonded to interface section 58. Molded packing 154 may be fabricated from the same types of materials suggested for molded packing 148. Plug 164 has been added to seal the proximal opening of outer sleeve 68a. Plug 164 is preferably created by forcing a sealing agent such as silicone or polyurethane into the proximal opening of outer sleeve 68a, or it may be a discrete plug formed from an elastomeric material. Alternatively, outer sleeve 68a may be crimped or welded at the end. Thus, the combination of plug 164, molded packing 154, and the seal between flexible tube 76 and interface section 58 creates a water-tight seal that prevents contaminating fluids from reaching the inner surfaces of flexible body 60. As with molded packing 148, molded packing 154 may take various forms, including, but not limited to, that of an O-ring. For example, an elastomeric diaphragm, analogous to flat diaphragm 166 discussed for sealing the distal end, may be utilized in place of molded packing 154. Similarly, a cylindrical plug formed from a closed-cell foam or resilient hydrophobic material, analogous to plug 168 discussed for sealing the distal end, may be used in place of molded packing 154. Alternatively, the entire lumen may be filled with a resilient material such as silicone, closed-cell foam or a gel-like substance, eliminating the space available for infiltrating fluids to accumulate.

Figure 28:
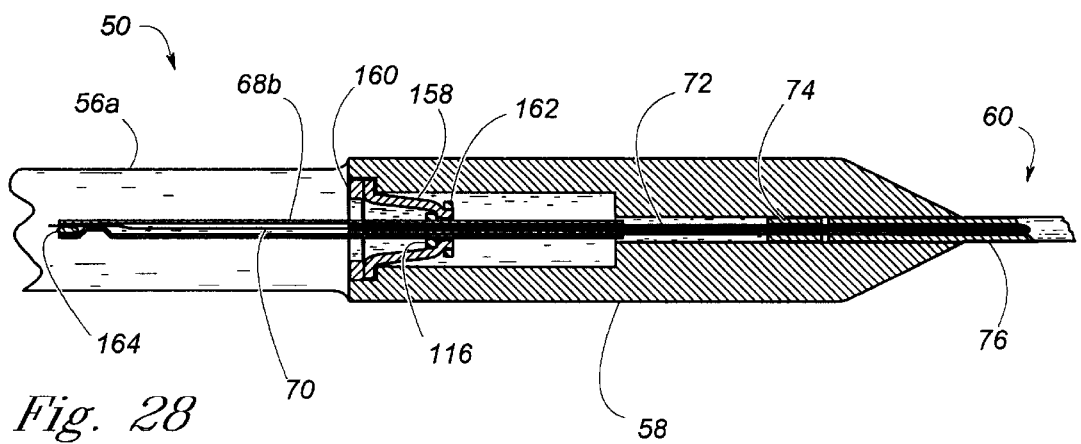
FIG. 28 is a modification of the control assembly illustrated in FIG. 2, incorporating a sealing boot therein.
Figure 29:
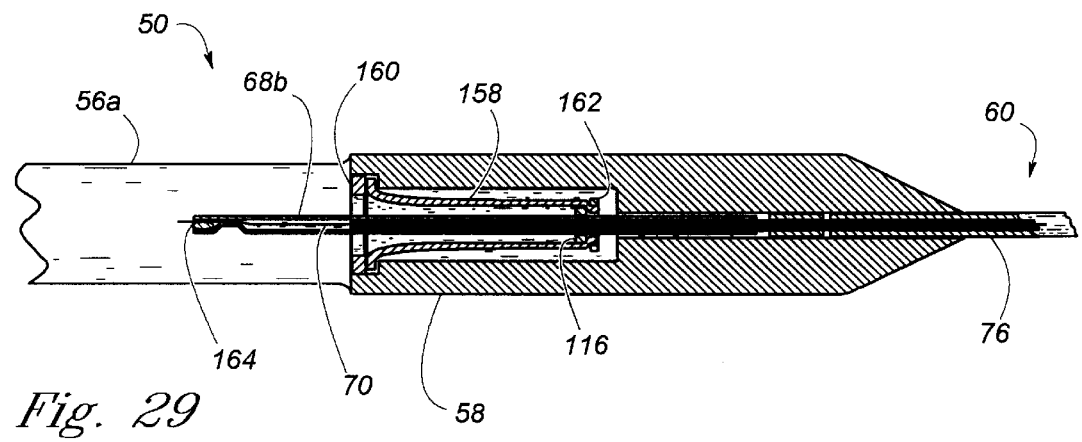
FIG. 29 shows the embodiment illustrated in FIG. 28, with the sealing boot fully stretched.

FIG. 28 shows a sectional side view of the embodiment illustrated in FIG. 27, with interface section 58 modified to accommodate sealing boot 158. Sealing boot 158 is secured at its proximal end by retaining ring 160 and at its distal end by the combination of collar 162 and raised rib 116 on outer sleeve 68b. Sealing boot 158 is preferably constructed of materials similar to those suggested for sealing boot 124. In the embodiment presented, the combination of plug 164, sealing boot 158, and the seal between flexible tube 76 and interface section 58 effectively prevents liquids from reaching the inner surfaces of flexible body 60. FIG. 29 shows sealing boot 158 fully stretched as outer sleeve 68b is advanced to its distal-most position. With the configuration shown in FIGS. 28 and 29, outer sleeve 68b, and thus control wire 70, return to their proximal-most position when control assembly 50 is released, thus biasing the jaws to their closed position. As discussed previously, this provides several advantages.

An alternative method of sealing the proximal end of the forceps device is disclosed in FIGS. 30 and 31. In this embodiment, the length of forked elements 56a and 56b has been reduced to the minimum length needed for cross-bar 64 to fully actuate the movable elements in the effector assembly. Forked elements 56a and 56b are shown in phantom in FIG. 30. By making the length of forked elements 56a and 56b shorter than the length of finger spool 54, molded packings 180a and 180b may be added, as shown in FIG. 31. Molded packings 180a and 180b are set in annular grooves on the inside surface of finger spool 54 and are sized to snugly squeeze against the outer surfaces of control assembly 50. The length of finger spool 54 is chosen to ensure that molded packings 180a and 180b always seal against a fully-radiused section of control assembly 50 and never travel onto forked elements 56a and 56b. By way of example, the length of forked elements 56a and 56b may be about 0.7 inches and the length of finger spool 54 may be about 1.5 inches. To further seal the control assembly, the interface between cross-bar 64 and finger spool 54 must be sealed either by a sealant such as silicone or by a tight press-fit between cross-bar 64 and finger spool 54. Sealing of set screw 66 within cross-bar 64 may be accomplished with a sealant such as silicone or by application of sealing tape to the thread of set screw 66. It will be appreciated that molded packings 180a and 180b, in combination with the seal between flexible tube 76 and interface section 58, and the seal between cross-bar 64 and finger spool 54 creates a water-tight seal that prevents contaminating fluids from reaching the inner surfaces of flexible body 60.

Many other sealing variants may be conceived at the proximal end. For example, a single molded packing at the proximal end of finger spool 54 may be combined with an outer sealing boot disposed between the distal end face of finger spool 54 and interface section 58. Similarly, a first sealing boot may be disposed between the proximal face of finger spool 54 and the base of thumb ring 52 and a second sealing boot may be disposed between the distal face of finger spool 54 and interface section 58. Such sealing boots could take various forms such as those discussed previously: a stretchable boot, a convoluted bellows or a rolling-type diaphragm. These embodiments may be further refined to bias finger spool 54 to a preferred orientation relative to interface section 58 when the control assembly is released. It will be appreciated that the objective of sealing the proximal end may also be attained by enshrouding the entire control assembly with a water-tight covering, such as a plastic bag. Likewise, adaptations of the embodiments presented are also possible which may involve unitary molding of elements described previously as being separate. For example, interface section 58 and finger spool 54 could be combined into a single, molded, sealed boot or bellows element and could include a biasing feature as previously described.

A forceps device incorporating a seal at both the distal end and proximal end would protect the lumen of flexible body 60 from infiltration by fluids. However, such a fully-sealed device would present several problems. First, initial sterilization of the device by the manufacturer would be more difficult. For example, if using a sterilizing agent such as ETO gas (ethylene oxide), the gas must be able to penetrate all areas of the device, and must likewise be vented from such areas before use on a patient. A tight seal at both ends of the device inhibits penetration of the gas into the lumen. Second, disinfection of the forceps device after use on a patient using steam autoclaving is problematic if the lumen is completely sealed. In a steam autoclave, the device is exposed to high pressure, causing a pressure difference between the outside of the forceps device and the lumen. For embodiments having significant volumes of trapped air within the lumen, such as those including elastomeric boots, this pressure difference can result in damage to the device.

A solution to the initial sterilization problem is to perform the sterilization step prior to the sealing of the lumen, followed by final assembly in a sterile environment. Alternatively, a vent hole may be added to the lumen to allow the passage of sterilizing gases. The vent hole would need to be sealed prior to removal of the device from the sterile environment. These approaches, however, would not solve the steam autoclave problem. By adding a hydrophobic barrier to the vent hole, sterilizing gases can pass into the lumen but contaminating fluids cannot. Such a hydrophobic barrier may be fabricated from a microporous membrane such as woven nylon or polyester available from Performance Systematix, Inc. (Caledonia, Mich.). Alternatively, the vent may be fitted with a valve means that can be activated manually or in response to a physical change such as temperature or pressure. Another solution is to employ the hydrophobic plug sealing means at either or both ends of the device, or to use the microporous membrane diaphragm, as previously described.

As can be seen from the foregoing embodiments directed at sealing means, the present invention represents a flexible forceps device which is easier to clean than prior art devices. Additional means may be employed to further simplify the cleaning process and to ensure that microbial growth is minimized. For example, the surfaces of flexible body 60 may be coated using a treatment such as Spi-Argent (trademark of Spire Corporation, Bedford, Mass.) which provides for a bactericidal and fungistatic surface with improved lubricity. A similar treatment may be applied to the metallic elements of effector assembly 62 and to the components of control assembly 50.

Further refinements of the effector assembly of the biopsy forceps embodiments disclosed are readily achieved. For example, FIGS. 32 to 34 illustrate an adaptation of the embodiment depicted in FIG. 8, showing apertures in the jaws and a needle element disposed between the jaws. The apertures relieve compressive pressure on tissue samples during jaw closure in order to minimize tissue trauma, while the needle element is used to spear tissue samples prior to closure of the jaws. FIG. 32 shows a side view of jaws 80*a* and 80*b* in their fully open position, with needle 136 disposed between them. FIG. 32A shows side and edge views of needle 136, illustrating mounting hole 138. FIG. 33 shows the same view as FIG. 32 with jaws 80*a* and 80*b* in their fully closed position, each jaw having an aperture 140*a* and 140*b*, respectively. Needle 136, shown in phantom, remains centered between jaws 80*a* and 80*b*. FIG. 34 is a top view of the embodiment illustrated in FIG. 33, with needle 136 shown in partial phantom. As can be seen, needle 136 is captured between jaws 80*a* and 80*b* onto riveted hinge-pin 100*b*. In FIG. 34A, riveted hinge-pin 100*b* is shown with a square mid-section sized to fit mounting hole 138 in needle 136. By securely bonding at least one end of riveted hinge-pin 100*b* to jaw support 78, so as to prevent rotation, needle 136 remains fixedly centered between jaws 80*a* and 80*b*.

Figure 35:
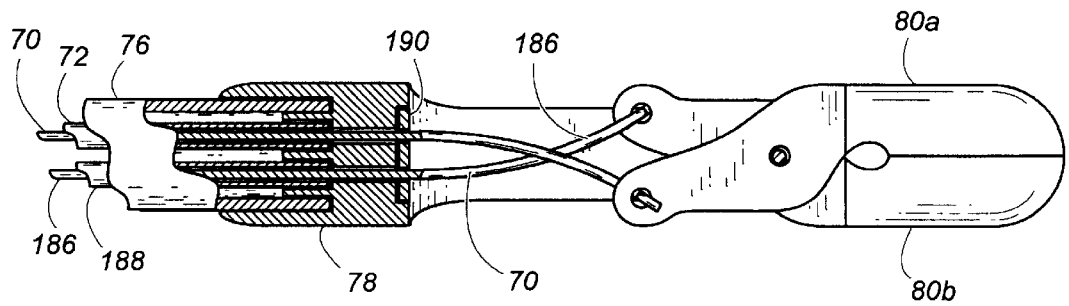
FIG. 35 is an enlarged side view of the effector assembly of a biopsy forceps device in accordance with a different embodiment of the invention, with portions broken away to illustrate the inner mechanisms.
Figure 35A:
FIG. 35a is a perspective view of the diaphragm element from the embodiment shown in FIG. 35.
Figure 36:
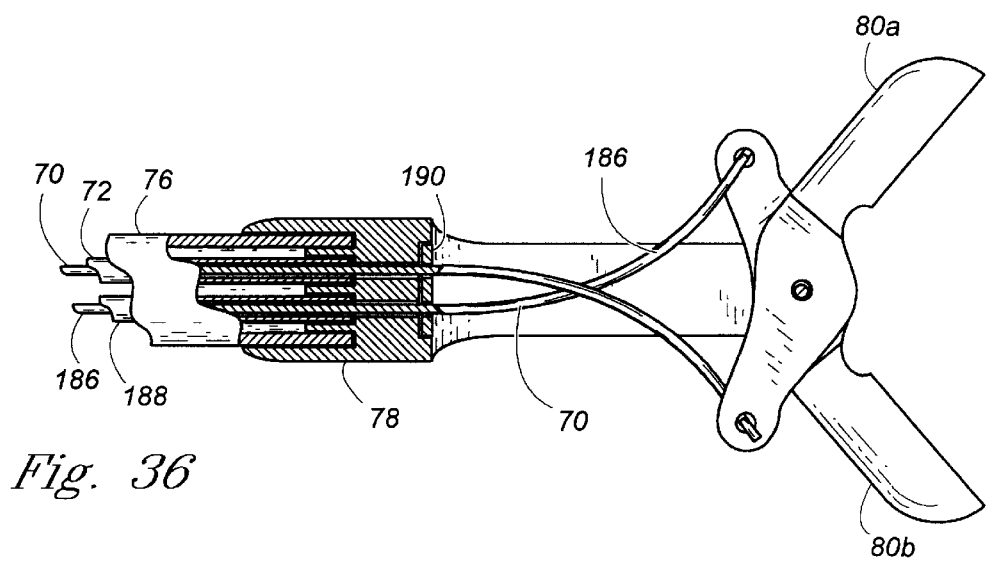
FIG. 36 is the same view illustrated in FIG. 35 with the jaws in their fully open position.

While the embodiments presented thus far illustrate forceps devices that utilize a single control wire, the novel coaxial actuator and sealing concepts are readily adapted to multiple control wire embodiments. As an example, FIGS. 35 and 36 show a side view of the distal region of a biopsy forceps having two coaxial actuator assemblies. The control wires from each coaxial actuating assembly individually actuate one of the jaws. In FIG. 35, the top coaxial actuating assembly is comprised of hollow tube 72 and control wire 70. Control wire 70 engages the lever hole of jaw 80*a*. The bottom coaxial actuator is comprised of hollow tube 188 and control wire 186. Control wire 186 engages the lever hole of jaw 80*b*. Jaw support 78 is adapted to provide an anchoring region for both hollow tubes 72 and 188, as well as an anchoring groove for flexible tube 76. As shown in FIG. 36, pushing on control wires 70 and 186 forces jaws 80*a* and 80*b* to open, respectively. The embodiment illustrated also incorporates an elastomeric diaphragm 190 having two holes whose diameters are slightly smaller than the diameters of control wires 70 and 186. Other sealing means such as molded packings and elastomeric boots are readily conceivable in this application. Adaptation of control assembly 50 to accommodate multiple coaxial actuators is also readily conceivable.

From the foregoing, it will be appreciated that the present invention provides a flexible forceps device with improvements in accordance with the above-described objects. While particular embodiments of the invention have been described, it is not intended that the invention be limited exactly thereto, as it is intended that the invention be as broad in scope as the art will permit. Thus, while a particular forceps device for retrieving biopsy samples is disclosed, it will be appreciated that other types of forceps instruments, such as graspers, dissectors, scissors and the like would be equally as appropriate applications for the improvements encompassing the present invention. Likewise, while the invention is disclosed for use with medical endoscopes, it is equally well-suited for use with industrial borescopes. Also, while various materials are described as being preferred for various parts, it will be appreciated that other materials could be utilized. Therefore, it will be apparent to those skilled in the art that other changes and modifications may be made to the invention as described in the specification without departing from the spirit and scope of the invention as so claimed.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

What is claimed is:

1. A flexible forceps device comprising:
   a flexible, elongated body with a lumen extending therethrough;
   a coaxial actuating assembly extending through said lumen of said flexible, elongated body, said coaxial actuating assembly consisting of:
      a flexible, hollow tube having a distal end and a proximal end with a lumen extending therethrough defining a long axis, said flexible, hollow tube being substantially incompressible along said long axis, and
      a control wire extending through said lumen of said flexible, hollow tube, said control wire having a distal end and a proximal end;
   an effector assembly attached to said distal end of said flexible, hollow tube, said effector assembly comprising:
      a support piece fixedly attached to said distal end of said flexible, hollow tube and the flexible, elongated body and the control wire, and
   at least one movable element linked to said support piece, said at least one movable element also being linked to said distal end of said control wire;
   a control means attached to the proximal end of said flexible, hollow tube, said control means configured to slidably move said control wire through said lumen of said flexible, hollow tube;
   wherein slidable movement of said control wire through said lumen of said flexible, hollow tube results in movement of said movable elements relative to said support piece, and
   wherein relatively little change in bending stiffness of the coaxial actuator assembly occurs over the full range of said movement of said control wire.

2. In a flexible forceps device according to claim 1 wherein said flexible, hollow tube is metal tubing.

3. In a flexible forceps device according to claim 2 wherein said metal tubing is stainless steel tubing.

4. In a flexible forceps device according to claim 3 wherein said stainless steel tubing is fabricated from flat stainless steel stock using a welding process.

5. In a flexible forceps device according to claim 4 wherein said welding process utilizes lasers to weld said stainless steel.

6. In a flexible forceps device according to claim 1 wherein said flexible, hollow tube has an outer diameter less than 0.025 inches.

7. In a flexible forceps device according to claim 1 wherein said flexible, elongated body, said support piece and said movable elements can be slidably inserted through a channel of an endoscope and operated therethrough.

8. In a flexible forceps device according to claim 1 wherein said movable elements comprise a pair of jaws.

9. In a flexible forceps device according to claim 8 wherein said support piece is configured to provide a hinge means for said jaws.

10. In a flexible forceps device according to claim 8 wherein said jaws are biopsy forceps jaws.

11. In a flexible forceps device according to claim 10 wherein a needle means is disposed between said jaws.

12. In a flexible forceps device according to claim 10 wherein said jaws each have a cup portion and an aperture disposed through said cup portion.

13. In a flexible forceps device according to claim 1 wherein said flexible, elongated body is a length of plastic tubing.

14. In a flexible forceps device according to claim 13 wherein the lubricity of the surface of said plastic tubing is increased by a surface treatment.

15. In a flexible forceps device according to claim 1 further comprising at least one additional said control wire or at least one additional said coaxial actuating assembly.

16. A coaxial actuating assembly comprising:
a flexible, hollow tube having a distal end and a proximal end with a lumen extending therethrough defining a long axis, said flexible, hollow tube being substantially incompressible along said long axis;
a control wire extending through said lumen of said flexible, hollow tube, said control wire having a distal end and a proximal end;
an effector means attached to said distal end of said flexible, hollow tube, said effector means also being linked to said distal end of said control wire;
wherein pulling on said proximal end of said control wire through said lumen of said flexible, hollow tube places said flexible, hollow tube in compression along said long axis of said flexible, hollow tube, and
wherein the bending stiffness of said coaxial actuating assembly changes relatively little when said compression is applied.

17. In a coaxial actuating assembly according to claim 16 wherein said flexible, hollow tube is metal tubing.

18. In a coaxial actuating assembly according to claim 17 wherein said flexible, hollow tube is stainless steel tubing.

19. In a coaxial actuating assembly according to claim 18 wherein said stainless steel tubing is fabricated from flat stainless steel stock using a welding process.

20. In a coaxial actuating assembly according to claim 19 wherein said welding process utilizes lasers to weld said stainless steel.

21. In a flexible forceps device according to claim 16 wherein said flexible, hollow tube has an outer diameter less than 0.025 inches.

22. A flexible forceps device comprising:
a flexible, elongated body having a distal end and a proximal end, said flexible, elongated body having a lumen extending therethrough;
an actuating means extending through said lumen of said flexible, elongated body, said actuating means having a distal end and a proximal end;
an effector assembly attached to said distal end of said flexible, elongated body, said effector assembly including at least one movable element, said movable element linked to said distal end of said actuating means;
a control means attached to the proximal end of said flexible, elongated body, said control means adapted to impart an actuating force to said proximal end of said actuating means;
wherein said actuating force is transmitted by said actuating means through said flexible, elongated body to said effector assembly to cause movement of said movable element;
said distal end of said flexible, elongated body being sealingly attached to said effector assembly;
said proximal end of said flexible, elongated body being sealingly attached to said control means;
sealing means disposed near at least one of said proximal or distal ends of said flexible, elongated body to prevent fluids from entering said lumen of said flexible, elongated body.

23. In a flexible forceps device according to claim 22 wherein said sealing means is comprised of a molded packing.

24. In a flexible forceps device according to claim 22 wherein said sealing means is comprised of a sealing boot.

25. In a flexible forceps device according to claim 22 wherein said sealing means is comprised of a diaphragm.

26. In a flexible forceps device according to claim 22 wherein said sealing means is a closed-cell foam plug.

27. In a flexible forceps device according to claim 22 wherein said sealing means is a plug made from hydrophobic material.

28. In a flexible forceps device according to claim 22 wherein said sealing means bias said movable elements to a preferred orientation when no external forces are applied to said control means.

29. In a flexible forceps device according to claim 22 wherein at least one of said flexible, elongated body, said support piece, said movable element, said sealing means and said control means is fabricated with surfaces that resist microbial growth.

30. In a flexible forceps device according to claim 22 wherein said sealing means are disposed near both the proximal and distal ends of said flexible, elongated body;
wherein the combination of said sealing means and said sealing attachments between said flexible body and both said support piece and said control means completely seal an interior space of said flexible forceps device;
said flexible forceps device further comprising venting means to allow the equilibration of air pressure between said interior space and the exterior atmosphere.

31. In a flexible forceps device according to claim 30 wherein said venting means includes a valve.

32. In a flexible forceps device according to claim 30 wherein said venting means incorporates filtering means to allow the passage of gas but not the passage of liquid.

33. In a flexible forceps device according to claim 32 wherein said filtering means comprises a hydrophobic element.

34. In a flexible forceps device according to claim 33 wherein said hydrophobic element is comprised of at least one of said sealing means.

35. In a flexible forceps device according to claim 22 wherein said actuating means is a coaxial actuating assembly comprising:
a flexible, hollow tube with a lumen extending therethrough defining a long axis, said flexible, hollow tube being substantially incompressible along said long axis, and
a control wire extending through said lumen of said flexible, hollow tube.

36. In a flexible forceps device according to claim 22 wherein said flexible, elongated body is fabricated from a material other than heat shrinkable tubing.

37. In a flexible forceps device according to claim 22 wherein said flexible, elongated body has a wall thickness of at least 0.020 inches.

38. In a flexible forceps device according to claim 22 wherein said sealing means are disposed near both the proximal and distal ends of said flexible, elongated body;
wherein said control means comprises a spool element with a relatively cylindrical bore slidably disposed around a relatively cylindrical portion of a shaft element, said spool element being attached to a point near said proximal end of said actuating means, said shaft element having a central bore surrounding a portion of said actuating means and being in sealing relationship with said proximal end of said flexible, elongated body, wherein slidable movement of said spool element along said shaft element imparts said actuating force to said proximal end of said actuating means, wherein said sealing means disposed near said proximal end of said flexible, elongated body comprises a seal between said spool element and said shaft element.

39. In a flexible forceps device according to claim 38 wherein said seal between said spool element and said shaft element is comprised of a pair of molded packings.

40. In a flexible forceps device according to claim 22 further comprising at least one additional said control wire or at least one additional said coaxial actuating assembly.

41. In a combination as set forth in claim 40, means for biasing the effector assembly to the first operative relationship when the effector assembly is not moved by the control wire to the second operative relationship, the effector assembly including a pair of jaws movable relative to each other between closed positions in the first relationship and open positions in the second relationship.

42. A flexible forceps device comprising:

a flexible, elongated body having a distal end and a proximal end, said flexible, elongated body having a lumen extending therethrough, said lumen defining a long axis of said flexible, elongated body;

an actuating means extending through said lumen of said flexible, elongated body, said actuating means having a distal end and a proximal end;

a control means attached to the proximal end of said flexible, elongated body, said control means linked to said proximal end of said actuating means;

a support piece attached to said distal end of said flexible, elongated body;

a lever element pivotally linked to said support piece, said lever element linked to said distal end of said actuating means;

at least one jaw element pivotally linked to said support piece;

a connecting means linking said lever element to said jaw element;

wherein manipulation of said control means causes said actuating means to transmit a force through said flexible, elongated body to said lever element, causing said lever element to pivot relative to said support piece, wherein said pivoting of said lever element causes movement of said connecting means resulting in pivoting of said at least one jaw element relative to said support piece.

43. In a flexible forceps device according to claim 42 wherein said actuating means is a coaxial actuating assembly comprising:

a flexible, hollow tube with a lumen extending therethrough defining a long axis, said flexible, hollow tube being substantially incompressible along said long axis, and a control wire extending through said lumen of said flexible, hollow tube.

44. In a flexible forceps device according to claim 43 wherein the centroidal long axis of said flexible, hollow tube of said coaxial actuating assembly is offset from the centroidal long axis of said flexible, elongated body.

45. In a flexible forceps device according to claim 42 wherein said at least one jaw element comprises a pair of jaws, and wherein said connecting means comprises a single connecting element.

46. In a flexible forceps device according to claim 45 wherein said single connecting element biases said pair of jaws to a preferred position when said control means is inactive.

47. In an actuating assembly, an incompressible tube having a lumen extending through the tube, a control wire extending through the lumen of the incompressible tube and movable along the lumen in the incompressible tube relative to the incompressible tube, and an effector assembly having first and second operative relationships, the effector assembly being operatively coupled to the control wire and the incompressible tube, wherein the effector assembly is movable between the first and second operative relationships by movement of the control wire along the lumen relative to the incompressible tube.

48. In an actuating assembly as set forth in claim 47, means for biasing the effector assembly to the first operative relationship when the effector assembly is not moved by the control wire to the second operative relationship.

49. In an actuating assembly as set forth in claim 47, the effector assembly including a pair of jaws movable relative to each other between closed positions in the first relationship and open positions in the second relationship.

50. In an actuating assembly as set forth in claim 47, means for retaining the incompressible tube in a fixed relationship at the first end of the tube to provide for a movement of the control wire relative to the tube through the lumen in the incompressible tube.

51. In an actuating assembly as set forth in claim 47, the control wire and the tube being made from stainless steel and the lumen extending longitudinally through the incompressible tube and the control wire extending longitudinally through the lumen in the incompressible tube.

52. In an actuating assembly as set forth in claim 47, the flexible tube being substantially incompressible in the longitudinal direction and the control wire being flexible.

53. In an actuating assembly as set forth in claim 47 wherein control means is disposed at a first end of the control wire and the incompressible tube for moving the control wire in the lumen in the incompressible tube relative to the incompressible tube and wherein the effector assembly is operatively coupled to the control wire and the incompressible tube at a second end of the control wire opposite the first end for operating the effector assembly in the first and second operative relationships in accordance with the movements of the control wire by the control means along the lumen in the flexible tube relative to the flexible tube.

54. In an actuating assembly, a flexible body having a lumen, a flexible tube disposed in the lumen in the body and having a lumen, a control wire extending through the lumen in the flexible tube and movable along the lumen in the tube relative to the flexible body and the flexible tube, the flexible body, the flexible tube and the control wire having first and second opposite ends, the flexible body and the flexible tube being disposed in a fixed relationship to each other, first means operatively coupled to the flexible tube and the control wire at the first ends of the flexible tube, the flexible body and the control wire for selectively providing a movement of the control wire in first and second opposite directions along the lumen in the flexible tube relative to the flexible tube and the flexible body, and second means operatively coupled to the flexible tube and the control wire at the second ends of the flexible tube and the control wire for respectively providing first and second operations in accordance with the selective movements of the control wire in the first and second opposite directions along the lumen in the tube relative to the flexible tube.

55. In an actuating assembly as set forth in claim 54, the lumens in the flexible body and in the tube extending in a longitudinal direction, and the first means providing a movement of the control wire in the longitudinal direction relative to the flexible tube, and the flexible tube being made from a material, and is, substantially incompressible in the longitudinal direction.

56. In an actuating assembly as set forth in claim 54, the second means including an effector assembly operative in first and second operative relationships and including means coupled to the flexible body, the control wire and the effector assembly for selectively providing an operation of the effector assembly in selective ones of the first and second relationships in accordance with the movements of the the control wire in the longitudinal direction relative to the flexible tube and the flexible body.

57. In an actuating assembly as set forth in claim 54 wherein the first means includes third means for holding the flexible body and the tube in the fixed relationship and fourth means movably disposed in the third means for moving the the control wire in the first and second opposite directions relative to the flexible tube and the flexible body.

58. In an actuating assembly as set forth in claim 56 wherein the second means includes support means having first and second operative relationships and operatively coupled to the flexible body and the flexible tube and the control wire and wherein the effector assembly includes at least one effector supported by the support means and operatively coupled to the control wire for providing a selective operation of the at least one effector in the first and second operative relationships in accordance with the selective movements of the control wire in the first and second opposite directions relative to the flexible tube.

59. In an actuating assembly as set forth in claim 58 wherein the lumens in the flexible body and in the tube respectively extend longitudinally through the flexible body and the flexible tube and wherein fourth means is operatively coupled to the control wire and is movable longitudinally in the first and second opposite directions to move the control wire selectively in the first and second longitudinal directions relative to the tube.

60. In an actuating assembly as set forth in claim 57 wherein the second means includes support means having first and second operative relationships and being operatively coupled to the flexible body and the flexible tube and the control wire wherein the effector assembly includes at least one effector supported by the support means and operatively coupled to the control wire for providing a selective operation of the at least one effector in the first and second operative relationships in accordance with the selective movements of the control wire in the first and second opposite directions relative to the flexible tube and wherein the lumens in the flexible body and in the tube respectively extend longitudinally through the flexible body and the flexible tube and wherein fourth means is operatively coupled to the control wire and is movable longitudinally in the first and second opposite directions to move the control wire selectively in the first and second longitudinal directions relative to the tube and wherein fifth means is disposed relative to the flexible body and the control wire for sealing the control wire relative to the flexible body to prevent a leakage of fluid into the space between the control wire and the flexible body.

61. In an actuating assembly as set forth in claim 54 wherein the second means includes support means having first and second operative relationships and operatively coupled to the flexible tube and the flexible body and the control wire and wherein the effector assembly includes at least one effector supported by the support means and operatively coupled to the control wire for providing a selective operation of the at least one effector in the first and second operative relationships in accordance with the selective movements of the control wire in the first and second opposite directions relative to the flexible tube.

62. In an actuating assembly as set forth in claim 54, third means for sealing the control wire relative to the flexible body to prevent a leakage of fluid into the space between the control wire and the flexible body.

63. In an actuating assembly as set forth in claim 54, the flexible tube being made from a material, and being, substantially incompressible in the longitudinal direction.

64. In an actuating assembly, a flexible tube having a lumen extending through the tube, a control wire extending through the lumen of the flexible tube and movable relative to the flexible tube along the lumen in the flexible tube, support means for the flexible tube, linkage means supported by the support means and having first and second operative relationships and operatively coupled to the control wire and to the flexible tube for operation in selective ones of the first and second relationships in accordance with the movement of the control wire in first and second opposite directions relative to the flexible tube, and an effector having first and second operative relationships and operatively coupled to the linkage means for selectively operating in the first and second relationships in accordance with the selective operation of the linkage means in the first and second relationships, wherein the linkage means is operative in the first and second relationships in accordance with the movements of the control wire along the lumen relative to the tube.

65. In an actuating assembly as set forth in claim 64, the effector constituting a forceps which is closed in the first operative relationship and which is open in the second operative relationship and the tube being substantially incompressible in the longitudinal direction.

66. In an actuating assembly as set forth in claim 64 wherein the linkage means includes a lever link having first and second ends and operatively coupled to the control wire at the first end and to the support means at the second end and includes a connector wire having first and second ends and wherein the effector includes first and second jaws and wherein the connector wire is connected to the first jaw at the first end of the connecting wire and to the second jaw at the second end of the connecting wire.

67. In an actuating assembly as set forth in claim 66 wherein the tube is made from a metal, and is, substantially incompressible in the longitudinal direction and wherein means is provided for retaining the tube in a fixed relationship at a first end of the tube to provide for the movement of the control wire relative to the tube by the control means.

68. In an actuating assembly as set forth in claim 64 wherein the linkage means includes first and second links each having first and second ends and wherein the links are pivotably connected to each other and to the control wire at the first end and wherein the effector includes first and second jaws and wherein the second ends of the first and second links are respectively connected to the first and second jaws at the second ends of the first and second jaws and wherein the tube is substantially incompressible in the longitudinal direction.

69. In an actuating assembly as set forth in claim 68, the tube is made from a metal, and is, substantially incompressible in the longitudinal direction and wherein means is provided for retaining the tube in a fixed relationship at a first end of the tube to provide for the movement of the control wire relative to the tube by the control means.

70. In an actuating assembly as set forth in claim 64 wherein the flexible tube is made from a metal, and is, substantially incompressible in the longitudinal direction.

71. In an actuating assembly as set forth in claim 64 wherein the flexible tube is made from a stainless steel and is substantially incompressible in the longitudinal direction.

72. In an actuating assembly as set forth in claim 64 including, means for retaining the flexible tube in a fixed relationship at a first end of the flexible tube to provide for the movement of the control wire relative to the flexible tube by the control means.

73. In an actuating assembly as set forth in claim 64, the linkage means being hingedly coupled to the support means and being movable with the control wire to change between the first and second operative relationships in accordance with the movement of the control wire along the lumen in the tube and the effector including first and second members hingedly connected to the linkage means and movable relative to each other between the first and second operative relationships in accordance with the change in the linkage means between the first and second operative relationships.

74. In an actuating assembly as set forth in claim 64, including, control means disposed at a first end of the control wire and the flexible tube and operatively coupled to the control wire and the flexible tube for moving the control wire along the lumen of the flexible tube in the first and second opposite directions without moving the flexible tube.

75. In an actuating assembly, a flexible body having a lumen, a flexible tube disposed in the lumen in the body and having a lumen, a control wire extending through the lumen in the tube, the flexible body and the control wire having first and second opposite ends, first means operatively coupled to the control wire, the flexible body and the flexible tube for moving the control wire relative to the flexible tube and the flexible body along the lumen in the flexible tube, and an effector assembly having first and second operative relationships and operatively coupled to the flexible tube for disposition within the flexible tube and operatively coupled to the control wire for movement between the first and second operative relationships in accordance with the movement of the control wire along the lumen in the flexible tube relative to the flexible body and the flexible tube, and second means for retaining the flexible body and the flexible tube in a fixed relationship.

76. In an actuating assembly as set forth in claim 75, a control assembly, the first means being included in the control assembly, and second means in the control assembly for providing a support for the retention of the flexible tube in the lumen in the flexible body and the retention of the control wire in the lumen in the flexible tube.

77. In an actuating assembly as set forth in claim 75, a control assembly having a first region for anchoring the flexible body in the control assembly and for supporting the flexible tube in the lumen in the flexible body and for supporting the control wire in the lumen in the flexible tube and having a second region displaced from the first region, the control assembly including a spool movable along the second region and holding the control wire for movement with the spool relative to the flexible body and the flexible tube.

78. In an actuating assembly as set forth in claim 77, the spool being shaped to receive at least one finger of the operator finger and the control assembly including a portion shaped to receive the operator's thumb.

79. In an actuating assembly as set forth in claim 78, a cross bar in the finger spool, and means extending into the cross bar for engaging the control wire to move the control wire with the finger spool relative to the flexible body and the flexible tube.

80. In an actuating assembly as set forth in claim 79, the flexible tube being substantially incompressible in the longitudinal direction.

81. In an actuating assembly as set forth in claim 75, means for sealing the control wire relative to the flexible body.

82. In an actuating assembly, a flexible body having a lumen, a flexible tube disposed in the lumen in the body and having a lumen, a control wire extending through the lumen in the flexible tube for movement along the lumen in the flexible tube relative to the flexible body and the flexible tube, support means operatively coupled to the flexible body and the flexible tube, linkage means supported by the support means and having first and second operative relationships and operatively coupled to the control wire for operation in selective ones of the first and second operative relationships in accordance with the movement of the control wire in first and second opposite directions, control means operatively coupled to the flexible body, the flexible tube and the control wire for disposing the body and the tube in a fixed relationship and for providing for a selective movement of the control wire in the first and second opposite directions along the lumen in the flexible tube relative to the flexible tube, and an effector having first and second operative relationships and operatively coupled to the linkage means for selective operation in the first and second relationships in accordance with the selective operation of the linkage means in the first and second operative relationships.

83. In an actuating assembly as set forth in claim 82 wherein the linkage means includes a lever link having first and second ends and operatively coupled to the control wire at the first end and to the support means at the second end and includes a connecting wire having first and second ends and the effector includes first and second jaws and wherein the connector wire is connected to the first jaw at the first end of the connector wire and to the second jaw at the second end of the connector wire.

84. In an actuating assembly as set forth in claim 83 wherein the connector wire extends to the lever link at an intermediate position between the first and second ends of the lever link.

85. In an actuating assembly as set forth in claim 83, the effector constituting a forceps which is closed in the first operative relationship and which is open in the second operative relationship, and the flexible tube being substantially incompressible.

86. In an actuating assembly as set forth in claim 82 wherein the linkage means includes first and second links each having first and second ends and wherein the links are pivotably connected to each other and to the control wire at the first end and wherein the effector includes first and second jaws and wherein the second ends of the first and second links are respectively connected to the first and second jaws at the second ends of the first and second jaws.

87. In an actuating assembly as set forth in claim 86 wherein the effector constitutes a forceps which is closed in the first operative relationship and which is open in the second operative relationship, and the tube being substantially in compressible in the longitudinal direction.

88. In an actuating assembly as set forth in claim 82, the linkage means being hingedly coupled to the control wire and being movable with the control wire to change between the first and second operative relationships in accordance with the movement of the control wire and the effector including first and second members hingedly connected to the linkage means and movable relative to each other between the first and second operative relationships in accordance with the change in the linkage means between the first and second operative relationships.

89. In an actuating assembly as set forth in claim 82, the control means including first means for disposing the flexible body and the flexible tube in the fixed relationship and including second means disposed in a co-operative relationship with the first means for providing a movement of the control wire in the first and second opposite directions relative to the flexible tube.

90. In an actuating assembly as set forth in claim 89, the first means including a thumb ring for holding at least one of an operator's fingers and the second means including a finger spool disposed on the first means for movement in the direction of the lumens in the flexible body and the flexible tube and shaped to receive one of the operator's fingers.

91. In an actuating assembly as set forth in claim 89 wherein the linkage means includes a lever link having first and second ends and operatively coupled to the control wire at the first end and to the support means at the second end and includes a connecting wire having first and second ends and wherein the effector includes first and second jaws and wherein the connector wire is connected to the first jaw at the first end of the connector wire and to the second jaw at the second end of the connector wire.

92. In an actuating assembly as set forth in claim 89, the linkage means includes first and second links each having first and second ends and wherein the first and second links are pivotably connected to each other and to the control wire at the first ends of the first and second links and wherein the effector includes first and second jaws and wherein the second ends of the first and second links are respectively connected to the first and second jaws and wherein the flexible tube is substantially incompressible in the longitudinal direction.

93. In an actuating assembly as set forth in claim 82, the control means including a first region for anchoring the flexible body and for anchoring the flexible tube in the lumen in the flexible body and for anchoring the control wire in the lumen in the tube and including a second region displaced from the first region, the control means also including a spool movable along the second region and holding the control wire for movement with the spool relative to the flexible body and the flexible tube.

94. In an actuating assembly, a flexible body having a lumen, a flexible tube disposed in the lumen in the flexible body and having a lumen, a control wire extending through the lumen in the flexible tube and movable in first and second opposite directions along the lumen in the flexible tube relative to the flexible body and the flexible tube, support means for the flexible body and the flexible tube, and an effector assembly supported by the support means and having first and second operative relationships and responsive to the movement of the control wire in the first direction along the lumen in the flexible tube relative to the flexible tube for providing an operation of the effector assembly in the first relationship and responsive to the movement of the control wire in the second direction along the lumen in the flexible tube relative to the flexible tube for providing an operation of the effector assembly in the second relationship, wherein the effector assembly is operative in the first and second relationships in accordance with the movement of the control wire along the lumen in the flexible tube relative to the flexible tube and the flexible body.

95. In an actuating assembly as set forth in claim 94, sealing means for providing a sealing relationship between the flexible body and the control wire.

96. In an actuating assembly as set forth in claim 95, the sealing means having first and second opposite ends and being coupled to the flexible body at the first end and to the control wire at the second end and having resiliently expansive properties to change shape in accordance with the movements of the control wire in the first and second opposite directions.

97. In an actuator assembly as set forth in claim 95, the sealing means including a packing member for sealing the flexible body and the control wire.

98. In an actuator assembly as set forth in claim 95, the sealing means including a diaphragm for sealing the flexible body and the control wire.

99. In an actuator assembly as set forth in claim 95, the sealing means including a plug made of a closed-cell foam or hydrophobic material for sealing the flexible body and the control wire.

100. In an actuating assembly as set forth in claim 95, a control assembly including a spool slidable in the control assembly and operatively coupled to the control wire for providing a movement of the control wire relative to the flexible tube along the lumen of the flexible tube.

101. In an actuating assembly as set forth in claim 100, the spool being shaped to receive at least one of an operator's fingers and the control assembly having a portion shaped at one end to receive the operator's thumb.

102. In an actuating assembly as set forth in claim 100, sealing means for providing a sealed relationship between the control assembly and the control wire.

103. In an actuating assembly as set forth in claim 100, sealing means for providing a sealed relationship between the control means and the control wire at a position adjacent the effector assembly.

104. In an actuating assembly as set forth in claim 94, control means operatively coupled to the flexible body, the flexible tube and the control wire for disposing the flexible body and the flexible tube in a fixed relationship and for providing for a selective movement of the control wire in first and second operative relationships along the lumen in the flexible tube relative to the flexible body and the flexible tube.

105. In an actuating assembly, a flexible body having a lumen, a flexible tube disposed in the lumen in the body and having a lumen, a control wire extending through the lumen in the flexible tube and movable along the lumen in the flexible tube relative to the flexible body and the flexible tube, control means operatively coupled to the flexible body, the flexible tube and the control wire for disposing the flexible body and the flexible tube in a fixed relationship and for providing for a selective movement of the control wire in first and second opposite directions along the lumen in the flexible tube relative to the flexible body and the flexible tube, an effector assembly supported by the support means and having first and second relationships and responsive to the movement of the control wire in the first direction along the lumen in the flexible tube relative to the flexible tube and the flexible body for providing a disposition of the effector assembly in the first relationship and responsive to the movement of the control wire in the second direction along the lumen in the flexible tube relative to the flexible wire and the flexible tube for providing a disposition of the effector assembly in the second relationship, and sealing means for providing a sealing relationship between the control means and the control wire.

106. In an actuating assembly as set forth in claim 105, the sealing means having first and second opposite ends and having resiliently expansive properties to change shape in accordance with the movements of the control wire in the first and second opposite directions along the lumen in the flexible tube relative to the flexible tube and the flexible body.

107. In an actuator assembly as set forth in claim 105, the sealing means including a packing member for sealing the control means and the tube.

108. In an actuator assembly as set forth in claim 105, the control means being included in a control assembly and the control assembly including a slidable spool operably coupled to the control wire for moving the control wire along the lumen in the flexible tube relative to the flexible tube in accordance with the slidable movement of the spool.

109. In an actuating assembly as set forth in claim 108, the slidable sleeve being shaped to receive at least one of an operator's fingers and the control assembly being shaped at a position further removed from the effector assembly than the spool to receive the operator's thumb.

110. In an actuating assembly as set forth in claim 105, the sealing means being disposed to provide the sealing relationship between the control means and the control at positions adjacent the effector assembly.

111. In an actuating assembly as set forth in claim 108, means for biasing the effector assembly to the first operative relationship when the effector assembly is not moved by the control wire to the second operative relationship, the flexible tube being substantially incompressible in the direction of the lumen in the flexible tube.

112. In an actuating assembly, a flexible body having a lumen, a flexible tube substantially incompressible in a longitudinal direction and having a lumen extending through the flexible tube, the tube being disposed in the lumen in the body, a control wire extending through the lumen in the flexible tube and movable along the lumen in the flexible tube relative to the flexible tube and the flexible body, first means operatively coupled to the flexible body and the flexible tube for disposing the flexible body and the flexible tube in a fixed relationship, second means disposed on the first means for slidable movement relative to the first means and operatively coupled to the control wire for moving the control wire along the lumen in the flexible tube relative to the flexible tube in accordance with the slidable movements of the second means, and an effector assembly having first and second operative relationships and operatively coupled to the flexible tube and the control and the flexible tube wire for selectively operating in the first relationship and in the second relationship in accordance with the movements of the control wire along the lumen in the flexible tube relative to the flexible tube.

113. In an actuating assembly as set forth in claim 112, third means for providing a sealing relationship between the first means and the control wire, the flexible tube being substantially incompressible in the longitudinal direction.

114. In an actuating assembly as set forth in claim 112, the first means including a lumen and the flexible body and the tube being anchored in the lumen in the first means and the second means including third means for anchoring the control wire to the second means.

115. In an actuating assembly as set forth in claim 114, the first means having a pair of elements defining a forked relationship and the third means being movable with the second means along the first means between the forked elements for anchoring the control wire to the second means for movement of the control wire with the second means along the first means.

116. In an actuating assembly as set forth in claim 115, the first means including a first portion shaped to receive an operator's thumb and the second means being shaped to receive at least one of an operator's fingers, the flexible tube being substantially incompressible in the longitudinal direction, and fourth means for providing a sealing relationship between the first means and the control wire.

117. In an actuating assembly as set forth in claim 114, the first means including a portion shaped to receive an operator's thumb and the second means being shaped to receive at least one of an operator's fingers, the flexible tube being substantially incompressible in the longitudinal direction.

118. In an actuating assembly as set forth in claim 114, fourth means for providing a sealing relationship between the first means and the control wire.

119. In an actuating assembly, a flexible body having a lumen, a flexible tube disposed in the lumen in the body and having a lumen, a control wire disposed in the lumen in the flexible tube and movable along the lumen in the tube relative to the flexible tube and the flexible body, first means for providing a movement of the control wire relative to the flexible body and the flexible tube along the lumen in the flexible tube, an effector assembly having first and second operative relationships, and second means operatively coupled to the control wire, the flexible body and the flexible tube and the effector assembly for providing a movement of the effector assembly between the first and second operative relationships in accordance with the movements of the control wire along the lumen in the flexible tube relative to the flexible body and the flexible tube.

120. In an actuating assembly as set forth in claim 119, the effector assembly including a pair of jaws having a closed disposition in the first relationship and an open disposition in the second relationship, the flexible tube being substantially incompressible in the longitudinal direction.

121. In an actuating assembly as set forth in claim 120, a pin, the pair of jaws being constructed to engage each other at the outer ends of the jaws and the jaws being disposed on the pin for pivotable movement relative to each other between the open and closed dispositions, and a needle disposed on the pin between the jaws to obtain a covering of the pin by the jaws with the jaws in the closed disposition and to obtain an exposure of the pin with the jaws in the open relationship.

122. In an actuating assembly as set forth in claim 119, the effector assembly also including linkage means having first and second operative relationships and operatively coupled to the control wire for selective operation in the first and second operative relationships in accordance with the movements of the control wire and also including a pair of jaws operatively coupled to the linkage means for movement relative to each other between open and closed positions in accordance with the selective operation of the linkage means in the first and second relationships.

123. In an actuating assembly as set forth in claim 122, each of the jaws in the pair having first and second ends and being operatively coupled to the linkage means at the first ends, a pin for holding the jaws at an intermediate position for pivotal movement, and the jaws being pivotable relative to each other between open and closed positions at their second ends.

124. In an actuating assembly as set forth in claim 123, a needle supported on the pin and extending to the second ends of the jaws, and the jaws being shaped to receive the pin in a nestled relationship with the jaws in the closed position of the jaws.

125. In an actuating assembly, a flexible body having a pair of lumens disposed in a spaced relationship and extending in substantially the same direction, a pair of flexible tubes each disposed in one of the lumens in the body and each having a lumen, a pair of control wires each disposed in the lumen in an individual one of the tubes and movable along the lumen in such individual one of tubes relative to the flexible body and the individual one of the flexible tubes, first means for holding the body and the flexible tubes in a fixed relationship, second means for providing movements of the control wires along the lumens in the flexible tubes relative to the flexible tubes and the flexible body, and an effector assembly having a pair of jaws each coupled to an individual one of the control wires for pivotable movements of the jaws relative to each other between open and closed positions in accordance with the movements of the control wires.

126. In an actuating assembly as set forth in claim 125, the control wires being connected to the jaws at first ends of the jaws, and a pin for holding the jaws at an intermediate position on the jaws and for providing a fulcrum at the intermediate position for pivotable movement of the jaws relative to each other.

127. In an actuating assembly as set forth in claim 125, the jaws being disposed on the pin for pivotable movement relative to each other between the open and closed positions in accordance with the movement of the control wires.

128. In an actuating assembly as set forth in claim 127, the effector assembly including a forceps and the jaws being included in the forceps and the flexible tubes being made from a material substantially incompressible in the longitudinal direction.

129. In an actuating assembly, a flexible body having a lumen in an offset relationship to the flexible body, a flexible tube disposed in the lumen in the body and having a lumen in the flexible tube, a control wire disposed in the lumen in the flexible tube and movable along the lumen in the flexible tube relative to the flexible body and the flexible tube, first means operatively coupled to the flexible body and the flexible tube for disposing the flexible body and the flexible tube in a fixed relationship to each other, second means operatively coupled to the control wire, the flexible tube and the flexible body for moving the control wire relative to the flexible tube along the lumen in the flexible tube and the flexible body, and an effector assembly having first and second operative relationships and connected to the flexible tube and operatively coupled to the control wire for providing a selective operation of the effector assembly in the first and second relationships in accordance with the movements of the control wire along the lumen in the flexible tube relative to the flexible tube and the flexible body.

130. In an actuating assembly as set forth in claim 129, the effector assembly including support means coupled to the flexible body and the flexible tube and including linkage means having first and second operative relationships and supported by the support means and operatively coupled to the control wire for selective operation of the linkage means to the first and second relationships in accordance with the movements of the control wire and including an effector having first and second operative relationships and operatively coupled to the linkage means for selective operation of the effector in the first and second relationships in accordance with the operation of the linkage means in the first and second relationships.

131. In an actuating assembly as set forth in claim 129, the flexible body and the flexible tube being anchored to the first means and the second means being slidable on the first means and being operatively coupled to the control wire to move the control wire relative to the flexible body and the flexible tube in accordance with such slidable movement.

132. In an actuating assembly as set forth in claim 129, the effector assembly including an effector having a pair of jaws pivotable relative to each other between open and closed positions and including means operatively coupled to the control wire and the jaws for selectively pivoting the jaws relative to each other between the open and closed positions in accordance with the movement of the control wire relative to the flexible wire and the flexible tube.

133. In an actuating assembly as set forth in claim 132, the flexible tube being anchored to the first means and the second means being slidable on the first means and being operatively coupled to the control wire to move the control wire relative to the flexible body and the flexible tube in accordance with such slidable movement, the first means being shaped to receive an operator's thumb and the second means being shaped to receive at least one of an operator's fingers.

134. In an actuating assembly as set forth in claim 129, the lumen in the flexible body constituting a first lumen, the flexible body having a second lumen in displaced relationship to the first lumen.

135. In an actuating assembly, a support, a first pair of lumens extending longitudinally in the support and displaced from each other in the support in a direction transverse to the longitudinal direction, a pair of tubes respectively extending longitudinally in the pair of lumens in the support, a second pair of lumens respectively extending longitudinally in the flexible tubes, a pair of control wires respectively extending longitudinally in the second pair of lumens and movable along the second pair of lumens relative to the flexible tubes and the flexible body, means disposed relative to the support and the pair of flexible tubes and the pair of control wires for moving the pair of control wires along the second pair of lumens relative to the flexible tubes, and an effector assembly including a pair of members respectively coupled operatively to the pair of control wires for moving the members relative to each other between first and second operative relationships in accordance with the movements of the control wires along the lumens in the tubes relative to the tubes.

136. In an actuator assembly as set forth in claim 135, the tubes and the control wires being flexible and the tubes being substantially incompressible in the longitudinal direction.

137. In an actuator assembly as set forth in claim 136, the moving means being movable in the longitudinal direction on the support and being operatively coupled to the pair of control wires to move the pair of control wires with the moving means and being shaped to receive at least one of an operator's fingers and the support including means for receiving an operator's thumb.

* * * * *